(12) United States Patent
Kossida et al.

(10) Patent No.: US 7,037,700 B2
(45) Date of Patent: May 2, 2006

(54) REGULATION OF HUMAN CERAMIDE KINASE

(75) Inventors: Sophia Kossida, Basel (CH); Jeffrey Encinas, Nara (JP); Eiko Takao, Nagasaki (JP)

(73) Assignee: Bayer Aktiengesellschaft, Leverkusen (DE)

( * ) Notice: Subject to any disclaimer, the term of this patent is extended or adjusted under 35 U.S.C. 154(b) by 310 days.

(21) Appl. No.: 10/631,958

(22) Filed: Dec. 19, 2003

(65) Prior Publication Data

US 2004/0192580 A1    Sep. 30, 2004

Related U.S. Application Data

(63) Continuation-in-part of application No. 09/969,896, filed on Oct. 4, 2001, now abandoned.

(60) Provisional application No. 60/314,113, filed on Aug. 23, 2001, provisional application No. 60/238,005, filed on Oct. 6, 2000.

(51) Int. Cl.
 *C12N 9/12* (2006.01)
 *C12N 15/00* (2006.01)
 *C12N 1/20* (2006.01)
 *C12Q 1/68* (2006.01)
 *C07K 1/00* (2006.01)

(52) U.S. Cl. .................. 435/194; 530/350; 435/252.3; 435/320.1; 435/6

(58) Field of Classification Search ............... 530/350; 435/194, 320.1, 252.3, 6
See application file for complete search history.

(56) References Cited

U.S. PATENT DOCUMENTS

2002/0082203 A1*   6/2002   Gerritsen et al. ............. 514/12
2003/0162206 A1*   8/2003   Sigiura et al. ................ 435/6

FOREIGN PATENT DOCUMENTS

| EP | 1 291 430 | 3/2003 |
| WO | WO 00/52173 A | 9/2000 |
| WO | WO 01/60990 A2 | 8/2001 |
| WO | WO 01/96575 A1 | 12/2001 |

OTHER PUBLICATIONS

ABSTRACT, Database EMBL 'Online, NIH-MGC: Database accession No. AW503999, XP002208102; Mar. 3, 2000.
ABSTRACT, Database EMBL 'Online, Bates K: Database accession No. Q9UGE5, XP002208103, May, 1, 2000.

* cited by examiner

*Primary Examiner*—Maryam Monshipouri
(74) *Attorney, Agent, or Firm*—Banner & Witcoff, Ltd.

(57) ABSTRACT

Reagents that regulate human ceramide kinase protein activity and reagents that bind to human ceramide kinase gene products can be used to regulate intracellular signaling and consequently cell proliferation and apoptosis. Such regulation is particularly useful for treating allergies including but not limited to asthma, autoimmune diseases such as rheumatoid arthritis, inflammatory disease, transplant rejection, and cancer, particularly lymphocytic leukemias, and could be a useful target of vaccination enhancing adjuvants. Central and peripheral nervous system disorders, such as Parkinson's disease, also can be treated.

5 Claims, 8 Drawing Sheets

FIG. 1

```
Q: 1       PKHLLVFINPFGGKGQGKRIYERKVAPLFTLASITTDIIGNKFYVNYVEVITEHANQAKE
           P..LL:.:NPFGG:G . : :..V.P:.: A.:: ::I TE..N.A:E
H: 144     PPRLLLLVNPFGGRGLAWQWCKNHVLPMISEAGLSFNLIQ----------TERQNHARE

TLYEINIDKYDGIVCVGGDGMFSEVLHGLIGRTQRSAGVDQNHPRAVLVPSSLRIGIIPA
           .:. :::..::DGIV.V.GDG:..EVL:GL:.R .: ..AV :P :GI:P.
           LVQGLSLSEWDGIVTVSGDGLLHEVLNGLLDR-------PDWEEAVKMP----VGILPC

GSTDCVCYS---------TVGTSDAETSALHIVVGDSLAMDVSSVHHNSTLLRYSVSLLG
           GS :.:. : .:G.. . ..:L :. G.. .:D: SV S :S. :.
           GSGNALAGAVNQHGGFEPALGLDLLLNCSLLLCRGGGHPLDLLSVTLASGSRCFSFLSVA

YGFYGDIIKDSEKKRWLGLARYDFSGLKTFLSHHCYEGTVSFLPAQHTVGSP 223
           :GF..D:  .SE: R LG AR:... :   ..: H.Y.G.:S:LPA. . .SP
           WGFVSDVDIQSERFRALGSARFTLGTVLGLATLHTYRGRLSYLPATVEPASP 352
```

FIG. 2

PKHLLVFINP FGGKGQGKRI YERKVAPLFT LASITTDIIG NKFYVNYVEV ITEHANQAKE TLYEINIDKY
DGIVCVGGDG MFSEVLHGLI GRTQRSAGVD QNHPRAVLVP SSLRIGIIPA GSTDCVCYST VGTSDAETSA
LHIVVGDSLA MDVSSVHHNS TLLRYSVSLL GYGFYGDIIK DSEKKRWLGL ARYDFSGLKT FLSHHCYEGT
VSFLPAQHTV GSPRDRKPCR AGCFVCRQSK QQLEEEQKKA LYGLEAAEDV EEWQVVCGKF LAINATNMSC
ACRRSPRGLS PAAHLGDGSS DLILIRKCSR FNFLRFLIRH TNQQDQ

REGULATION OF HUMAN CERAMIDE KINASE

This application is a continuation-in-part of application Ser. No. 09/969,896 filed Oct. 4, 2001 now abandoned, which claims priority to provisional applications Ser. Nos. 60/238,005 filed Oct. 6, 2000 and 60/314,113 filed Aug. 23, 2001. Each of these applications is incorporated herein by reference in its entirety.

FIELD OF THE INVENTION

The invention relates to the area of regulation of intracellular signaling. More particularly, the invention relates to the regulation of human ceramide kinase activity to increase or decrease intracellular signaling.

BACKGROUND OF THE INVENTION

Human ceramide kinase demonstrates phosphorylating activity against ceramide type sphingolipids. The activity is dependent upon the length of the fatty acyl moiety, with longer chain ceramides generally being phosphorylated at a higher rate than shorter chain ceramides. As chain length increases and ceramides become increasingly more difficult to solubilize, however, phosphorylation activity decreases along with the decrease in solubility. The difference in phosphorylation rates between the long and short chain ceramides does not appear to be due to slower dissociation rates for the shorter chain ceramides since mixing shorter chain ceramides with longer chain ceramides (for example C2 ceramide with C8 ceramide; or C0 ceramide (sphingosine) with C2 ceramide) does not appear to significantly affect phosphorylation rates of the longer species.

Ceramide, the central molecule in the sphingomyelin pathway, serves as a second messenger for cellular functions ranging from differentiation to growth arrest and apoptosis. Ceramide signaling contributes to several aspects of immune cell function. It is a second messenger for the cytokine TNFα, IL-1β, IFNγ, and has been implicated in the signaling pathways of several lymphocyte surface proteins. Following its generation, ceramide can be converted to sphingosine, phosphorylated to ceramide-1-phosphate, converted to sphingomyelin, or glycosylated to form glycosphingolipids. It can also act without conversion by interacting directly with proteins downstream in the signaling cascade. One of the most well studied downstream effects of ceramide signaling is apoptosis. Ceramide is an important mediator of many of the cell surface receptors involved in transmitting death signals into cells, particularly receptors of the TNF receptor superfamily.

Possibly as a negative feedback mechanism to counter ceramide-mediated cell death, sphingosine-1-phosphate, generated after conversion of ceramide to sphingosine by ceramidase and then phosphorylation of sphingosine by sphingosine kinase, can promote cell survival. Sphingosine-1-phosphate released by cells can act as a potent agonist of cell-surface receptors of the EDG receptor family, among others, and prevent cell death initiated by a various apoptosis-inducing treatments. Sphingosine-1 phosphate has also been reported to act as a growth and differentiation factor.

There is a need in the art for identifying new ceramide kinase proteins and methods of regulating intracellular signaling and apoptosis.

BRIEF SUMMARY OF THE INVENTION

It is an object of the invention to provide reagents and methods of regulating intracellular signalling. These and other objects of the invention are provided by one or more of the embodiments described below.

One embodiment of the invention is a cDNA encoding a polypeptide comprising an amino acid sequence selected from the group consisting of (a) the amino acid sequences shown in SEQ ID NOS:2, 10, and 11 and (b) biologically active variants thereof Another embodiment of the invention is an expression vector comprising a polynucleotide which encodes a polypeptide comprising an amino acid sequence selected from the group consisting of (a) the amino acid sequences shown in SEQ ID NOS:2, 10, and 11 and (b) biologically active variants thereof.

Yet another embodiment of the invention is a host cell comprising an expression vector which encodes a polypeptide comprising an amino acid sequence selected from the group consisting of (a) the amino acid sequences shown in SEQ ID NOS:2, 10, and 11 and (b) biologically active variants thereof Even another embodiment of the invention is a purified polypeptide comprising an amino acid sequence selected from the group consisting of (a) the amino acid sequences shown in SEQ ID NOS:2, 10, and 11 and (b) biologically active variants thereof.

Still another embodiment of the invention is a fusion protein comprising a polypeptide consisting of an amino acid sequence selected from the group consisting of (a) the amino acid sequence shown in SEQ ID NOS:2, 10, or 11 and (b) biologically active variants thereof Another embodiment of the invention is a method of producing a polypeptide comprising an amino acid sequence selected from the group consisting of (a) an amino acid sequence selected from the group consisting of SEQ ID NOS:2, 10, and 11 and (b) biologically active variants thereof, comprising the steps of culturing a host cell comprising an expression vector that encodes the polypeptide under conditions whereby the polypeptide is expressed; and isolating the polypeptide.

Yet another embodiment of the invention is a method of detecting a coding sequence for a polypeptide comprising an amino acid sequence selected from the group consisting of (a) the amino acid sequences shown in SEQ ID NOS:2, 10, and 11 and (b) biologically active variants thereof, comprising the steps of hybridizing a polynucleotide comprising 11 contiguous nucleotides selected from the group consisting of (a) the complement of a nucleotide sequence selected from the group consisting of SEQ ID NOS:1 and 9, (b) a polynucleotide that hybridizes under stringent conditions to (a), (c) a polynucleotide having a nucleic acid sequence that deviates from the nucleic acid sequences specified in (a) and (c) due to the degeneration of the genetic code, and (d) a polynucleotide that represents a fragment, derivative, or allelic variation of a nucleic acid sequence specified in (a) to (c) to nucleic acid material of a biological sample to form a hybridization complex; and detecting the hybridization complex.

Still another embodiment of the invention is a kit for detecting a coding sequence for a polypeptide comprising an amino acid sequence selected from the group consisting of (a) an amino acid sequence selected from the group consisting of SEQ ID NOS:2, 10, and 11 and (b) biologically active variants thereof, comprising a polynucleotide comprising 11 contiguous nucleotides selected from the group consisting of (a) the complement of a nucleotide sequence selected from the group consisting of SEQ ID NOS:1 and 9, (b) a polynucleotide that hybridizes under stringent conditions to (a), (c) a polynucleotide having a nucleic acid sequence that deviates from the nucleic acid sequences specified in (a) and (c) due to the degeneration of the genetic code, and (d) a polynucleotide that represents a fragment, derivative, or allelic variation of a nucleic acid sequence specified in (a) to (c); and instructions for a method of detecting the coding sequence.

Even another embodiment of the invention is a method of detecting a polypeptide comprising an amino acid sequence selected from the group consisting of (a) the amino acid sequences shown in SEQ ID NOS:2, 10, and 11 and (b) biologically active variants thereof, comprising the steps of contacting a biological sample with a reagent that specifically binds to the polypeptide to form a reagent-polypeptide complex; and detecting the reagent-polypeptide complex.

Yet another embodiment of the invention is a kit for detecting a polypeptide comprising an amino acid sequence selected from the group consisting of (a) an amino acid sequence selected from the group consisting of SEQ ID NOS:2, 10, and 11, and (b) biologically active variants thereof, comprising an antibody which specifically binds to the polypeptide; and instructions for a method of detecting the polypeptide.

Still another embodiment of the invention is a method of screening for agents that can regulate an activity of a human ceramide kinase protein, comprising the steps of contacting a test compound with a polypeptide comprising an amino acid sequence selected from the group consisting of (a) the amino acid sequences shown in SEQ ID NOS:2, 10, and 11 and (b) biologically active variants thereof; and detecting binding of the test compound to the polypeptide, wherein a test compound that binds to the polypeptide is identified as a potential agent for regulating the activity of the human ceramide kinase protein.

Yet another embodiment of the invention is a method of screening for therapeutic agents that can regulate an enzymatic activity of a human ceramide kinase protein, comprising the steps of contacting a test compound with a polypeptide comprising an amino acid sequence selected from the group consisting of (a) the amino acid sequences shown in SEQ ID NOS:2, 10, and 11 and (b) biologically active variants thereof; and detecting the enzymatic activity of the polypeptide, wherein a test compound that increases the enzymatic activity of the polypeptide is identified as a potential therapeutic agent for increasing the enzymatic activity of the human ceramide kinase protein, and wherein a test compound that decreases the enzymatic activity of the polypeptide is identified as a potential therapeutic agent for decreasing the enzymatic activity of the human ceramide kinase protein.

A further embodiment of the invention is a method of screening for therapeutic agents that can regulate an activity of a human ceramide kinase protein, comprising the steps of contacting a test compound with a product encoded by a polynucleotide comprising a nucleotide sequence selected from the group consisting of (a) the amino acid sequences shown in SEQ ID NOS:2, 10, and 11 and (b) biologically active variants thereof; and detecting binding of the test compound to the product, wherein a test compound that binds to the product is identified as a potential therapeutic agent for regulating the activity of the human ceramide kinase protein.

Another embodiment of the invention is a method of reducing an activity of a human ceramide kinase protein, comprising the step of contacting a cell comprising the human ceramide kinase protein with a reagent that specifically binds to a product encoded by a polynucleotide comprising a nucleotide sequence selected from the group consisting of (a) the amino acid sequences shown in SEQ ID NOS:2, 10, and 11 and (b) biologically active variants thereof, whereby the activity of the human ceramide kinase protein is reduced.

Even another embodiment of the invention is a pharmaceutical composition, comprising a reagent that specifically binds to a polypeptide comprising an amino acid sequence selected from the group consisting of (a) amino acid sequences shown in SEQ ID NOS:2, 10, and 11 and (b) biologically active variants thereof; and a pharmaceutically acceptable carrier.

Still another embodiment of the invention is a pharmaceutical composition, comprising a reagent that specifically binds to a product of a polynucleotide comprising a coding sequence selected from the group consisting of (a) the amino acid sequences shown in SEQ ID NOS:2, 10, and 11 and (b) biologically active variants thereof; and a. pharmaceutically acceptable carrier.

Yet another embodiment of the invention is a pharmaceutical composition, comprising an expression vector encoding a polypeptide comprising an amino acid sequence selected from the group consisting of (a) the amino acid sequences shown in SEQ ID NOS:2, 10, and 11 and (b) biologically active variants thereof; and a pharmaceutically acceptable carrier.

A further embodiment of the invention is a method of treating a disorder selected from the group consisting of a cancer, an allergy, a CNS disorder, and an autoimmune disease, comprising the step of administering to a patient in need thereof a therapeutically effective dose of a reagent that inhibits a function of a human ceramide kinase protein, wherein the human ceramide kinase protein comprises an amino acid sequence selected from the group consisting of (a) the amino acid sequences shown in SEQ ID NOS:2, 10, and 11 and (b) biologically active variants thereof, whereby symptoms of the disorder are ameliorated.

Another embodiment of the invention is an isolated polynucleotide selected from the group consisting of: (a) a polynucleotide encoding a protein that comprises the amino acid sequence of SEQ ID NO:2, 10, or 11, (b) a polynucleotide comprising a sequence selected from the group consisting of SEQ ID NOS:1 and 9, (c) a polynucleotide which hybridizes under stringent conditions to a polynucleotide specified in (a) or (b); (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

Still another embodiment of the invention is an expression vector comprising an isolated polynucleotide selected from the group consisting of: (a) a polynucleotide encoding a protein that comprises the amino acid sequence of SEQ ID NO:2, 10, or 11, (b) a. polynucleotide comprising a sequence selected from the group consisting of SEQ ID NOS:1 and 9, (c) a polynucleotide which hybridizes under stringent conditions to a polynucleotide specified in (a) or (b); (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

Even another embodiment of the invention is a host cell comprising an expression vector comprising an isolated polynucleotide selected from the group consisting of: (a) a polynucleotide encoding a protein that comprises the amino acid sequence of SEQ ID NO:2, 10, or 11, (b) a polynucleotide comprising a sequence selected from the group consisting of SEQ ID NOS:1 and 9, (c) a polynucleotide which hybridizes under stringent conditions to a polynucleotide specified in (a) or (b); (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

A further embodiment of the invention is a preparation of antibodies that specifically bind to a polypeptide selected from the group consisting of (a) the amino acid sequence shown in SEQ ID NO:2, 10, or 11 and (b) biologically active variants thereof.

Still another embodiment of the invention is an antisense oligonucleotide that hybridizes to a polynucleotide selected from the group consisting of (a) a polynucleotide encoding a protein that comprises the amino acid sequence of SEQ ID NO:2, 10, or 11, (b) a polynucleotide comprising a nucleotide sequence selected from the group consisting of SEQ ID NOS:1 and 9, (c) a polynucleotide which hybridizes under stringent conditions to a polynucleotide specified in (a) or (b), (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

The invention thus provides reagents and methods for regulating intracellular signaling, which can be used, inter alia, to suppress metastatic activity and proliferation of. malignant cells and to treat autoimmune diseases, allergies, CNS disorders, inflammatory disease, transplant rejection, and lymphocytic leukemias.

BRIEF DESCRIPTION OF THE DRAWINGS

FIG. 1. BLASTP alignment of human ceramide kinase (SEQ ID NO:2) against tremblnew|AF245447|AF245447_1 product (SEQ ID NO:3), Sphigosine_kinase against: "sphingosine kinase type 2 isoform"; Homo sapiens sphingosine kinase type 2 isoform mRNA, complete cds. //:gp|AF245447|8248285 product: "sphingosine kinase type 2 isoform"; Homo sapiens sphingosine kinase type 2 isoform mRNA, complete cds. //:gpnew|AF245447|8248285 product: "sphingosine kinase type 2 isoform"; Homo sapiens sphingosine kinase type 2 isoform mRNA, complete cds. This hit is scoring at: 1e-17 (expectation value) Alignment length (overlap): 232 Identities: 28% Scoring matrix: BLOSUM62 (used to infer consensus pattern). Database searched was: nrdb. Diacylglycerol kinase catalytic domain is shown in bold.

FIG. 2. Amino acid sequence of human ceramide kinase (SEQ ID NO:2). The diacylglycerol kinase catalytic domain is shown in bold.

DETAILED DESCRIPTION OF THE INVENTION

Figure 3:
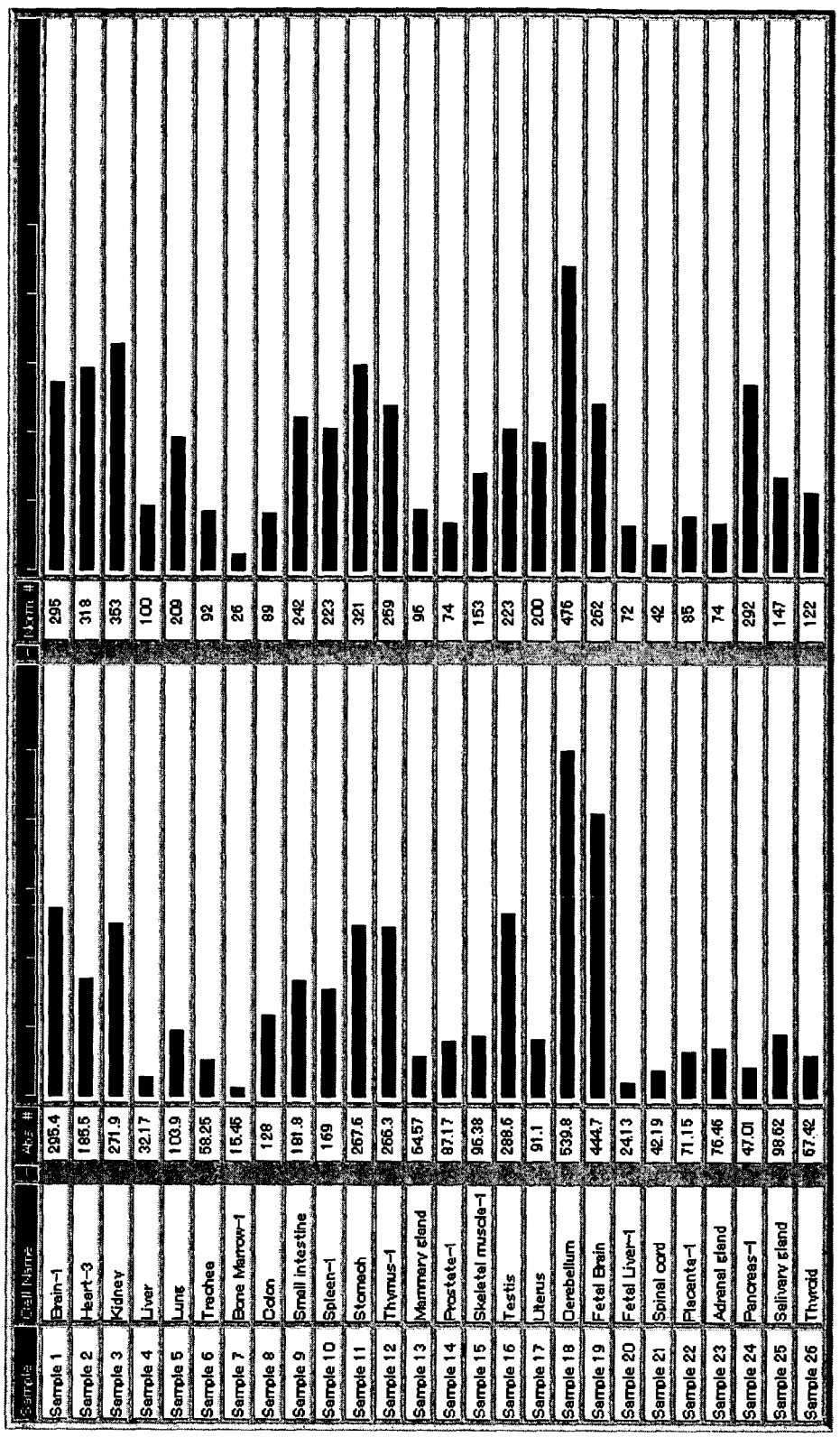
FIG. 3. Expression profiling of human ceramide kinase (SEQ ID NO:10), whole body screen.

The human ceramide kinases of the invention have the amino acid sequences shown in SEQ ID NOS:2, 10, and 11. SEQ ID NO:2 is 28% identical over 232 amino acids to the Homo sapiens protein identified by EMBL Accession No. AF245447 (SEQ ID NO:3) and annotated as a putative amine oxidase (FIG. 1). Human ceramide kinase protein contains a diacylglycerol kinase domain, which is shown in bold in FIG. 2.

A coding sequence for SEQ ID NO:2 is shown in SEQ ID NO:1. A coding sequence for SEQ ID NOS:10 and 11 is shown in SEQ ID NO:9. This sequence is contained within the longer sequence shown in SEQ ID NO:16. Related ESTs (SEQ ID NOS: 4–8) are expressed in germinal center B lymphocytes, T-lymphocytes, embryonic tissue, neuroblastoma, liver, ovary, brain, and kidney.

Regulators of a human ceramide kinase can be used to regulate intracellular signaling. Human ceramide kinase is expected to be especially useful for treating allergic disease, inflammatory disease, autoimmune disease, transplant rejection, and lymphocytic leukemias, and could be a useful target of vaccination enhancing adjuvants.

Polypeptides

Ceramide kinase polypeptides according to the invention comprise an amino acid sequence as shown in SEQ ID NO:2, a portion of SEQ ID NO:2 comprising at least 6, 10, 15, 25, 50, 75, 100, 125, 150, 175, 200, 225, 250, 275, 300, 320, or 326 contiguous amino acids, or a biologically active variant of the amino acid sequence shown in SEQ ID NO:2, as defined below. Ceramide kinase polypeptides according to the invention also can comprise an amino acid sequence as shown in SEQ ID NO:10, a portion of SEQ ID NO:10 comprising at least 6, 10, 15, 25, 50, 75, 100, 125, 150, 175, 200, 225, 250, 275, 300, 325, 350, 375, 400, 425, 450, 475, 500, 525, or 537 contiguous amino acids, or a biologically active variant of the amino acid sequence shown in SEQ ID NO:10, as defined below, the amino acid sequence as shown in SEQ ID NO:11, a portion of SEQ ID NO:11 comprising at least 6, 10, 15, 25, 50, 75, 100, 125, 150, 175, 200, 225, 250, 275, 300, 325, 350, 375, 400, 425, 450, 475, 500, 525, 550, or 562 contiguous amino acids, or a biologically active variant of the amino acid sequence shown in SEQ ID NO:11, as defined below. A ceramide kinase polypeptide of the invention therefore can be a portion of a ceramide kinase molecule, a full-length ceramide kinase molecule, or a fusion protein comprising all or a portion of a ceramide kinase molecule.

Biologically Active Variants

Ceramide kinase protein variants that are biologically active, i.e., retain a ceramide kinase activity, also are ceramide kinase polypeptides. Preferably, naturally or non-naturally occurring ceramide kinase variants have amino acid sequences which are at least about 30, 35, 40, 45, 50, 55, 60, 65, 70, preferably about 75, 90, 96, or 98% identical to an amino acid sequence shown in SEQ ID NO:2, 10, or 11.

Percent identity between a putative human ceramide kinase polypeptide variant and an amino acid sequence of SEQ ID NO:2 is determined by conventional methods. See, for example, Altschul et al., *Bull. Math. Bio*. 48:603 (1986), and Henikoff & Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff & Henikoff, 1992.

Those skilled in the art appreciate that there are many established algorithms available to align two amino acid sequences. The "FASTA" similarity search algorithm of Pearson & Lipman is a suitable protein alignment method for examining the level of identity shared by an amino acid sequence disclosed herein and the amino acid sequence of a putative variant. The FASTA algorithm is described by Pearson & Lipman, *Proc. Nat'l Acad. Sci. USA* 85:2444 (1988), and by Pearson, *Meth. Enzymol*. 183:63 (1990). Briefly, FASTA first characterizes sequence similarity by identifying regions shared by the query sequence (e.g., SEQ ID NO: 2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired: amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman & Wunsch, *J. Mol. Biol*. 48:444 (1970); Sellers, *SIAM J. Appl. Math*.26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol*. 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine. Ceramide kinase polypeptides of the invention can have, for example, 1, 2, 3, 4, 5, 6, 7, 8, 9, or 10 conservative amino acid substitutions relative to SEQ ID NOS:2, 10, or 11.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a human ceramide kinase polypeptide can be found using computer programs well known in the art, such as DNASTAR software.

The invention additionally, encompasses ceramide kinase polypeptides that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques including, but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The ceramide kinase polypeptides may also be modified with a detectable label, such as an enzymatic, fluorescent, isotopic or affinity label to allow for detection and isolation of the protein.

The invention also provides chemically modified derivatives of ceramide kinase polypeptides that may provide additional advantages such as increased solubility, stability and circulating time of the polypeptide, or decreased immunogenicity (see U.S. Pat. No. 4,179,337). The chemical moieties for derivitization can be selected from water soluble polymers such as polyethylene glycol, ethylene glycol/propylene glycol copolymers, carboxymethylcellulose, dextran, polyvinyl alcohol, and the like. The polypeptides can be modified at random or predetermined positions within the molecule and can include one, two, three, or more attached chemical moieties. Whether an amino acid change results in a biologically active ceramide kinase polypeptide can readily be determined by assaying for ceramide kinase activity, as is known in the art and described, for example, in J Biol Chem. 1990 Nov 5;265(31):18803–8.

Fusion Proteins

Fusion proteins are useful for generating antibodies against ceramide kinase amino acid sequences and for use in various assay systems. For example, fusion proteins can be used to identify proteins that interact with portions of a ceramide kinase polypeptide, including its active site. Methods such as protein affinity chromatography or library-based assays for protein-protein interactions, such as the yeast two-hybrid or phage display systems, can be used for this purpose. Such methods are well known in the art and also can be used as drug screens.

A ceramide kinase fusion protein comprises two protein segments fused together by means of a peptide bond. Contiguous amino acids for use in a fusion protein can be selected from the amino acid sequence shown in SEQ ID NO:2 or from a biologically active variants of those sequences, such as those described above. For example, the first protein segment can comprise at least 6, 10, 15, 25, 50, 75, 100, 125, 150, 175, 200, 225, 250, 275, 300, 325, or 340 or more contiguous amino acids of SEQ ID NO:2 or a biologically active variant, at least 6, 10, 15, 25, 50, 75, 100, 125, 150, 175, 200, 225, 250, 275, 300, 325, 350, 375, 400, 425, 450, 475, 500, 525, or 537 contiguous amino acids of SEQ ID NO:10 or a biologically active variant, or at least 6, 10, 15, 25, 50, 75, 100, 125, 150, 175, 200, 225, 250, 275, 300, 325, 350, 375, 400, 425, 450, 475, 500, 525, 550, or 562 contiguous amino acids of SEQ ID NO:11 or a biologically active variant. In one embodiment, a fusion protein comprises the active site of the kinase. The first protein segment also can comprise full-length ceramide kinase.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose-binding protein (MBP), S-tag, Lex a DNA binding domain (DBD) fusions, GAL4 DNA binding domain fusions, and herpes simplex virus (HSV) BP16 protein fusions. A fusion protein also-can be engineered to contain a cleavage site located between the ceramide kinase polypeptide-encoding sequence and the heterologous protein sequence, so that the ceramide kinase polypeptide can be cleaved and purified away from the heterologous moiety.

A fusion protein can be synthesized chemically, as is known in the art. Preferably, a fusion protein is produced by covalently linking two protein segments or by Standad procedures in the art of molecular biology. Recombinant DNA methods can be used to prepare fusion proteins, for example, by making a DNA construct which comprises ceramide kinase protein coding sequences disclosed herein in proper reading frame with nucleotides encoding the second protein segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human ceramide kinase can be obtained using ceramide kinase polynucleotides (described below) to make suitable probes or primers to screening cDNA expression libraries from other species, such as mice, monkeys, or yeast, identifying cDNAs which encode homologs of ceramide kinase, and expressing the cDNAs as is known in the art.

Polynucleotides

A ceramide kinase polynucleotide can be single- or double-stranded and comprises a coding sequence or the complement of a coding sequence for a ceramide kinase polypeptide. Coding sequences are shown in SEQ ID NOS:1 and 9.

Degenerate nucleotide sequences encoding human ceramide kinase polypeptides, as well as homologous nucleotide sequences which are at least about 50, 55, 60, 65, 70, preferably about 75, 90, 96, or 98% identical to the ceramide kinase coding sequences nucleotide sequence shown in SEQ ID NOS:1 and 9 also are ceramide kinase polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of ceramide kinase polynucleotides which encode biologically active ceramide kinase polypeptides also are ceramide kinase polynucleotides.

Identification of Variants and Homologs

Variants and homologs of the ceramide kinase polynucleotides disclosed above also are ceramide kinase polynucleotides. Typically, homologous ceramide kinase polynucleotide sequences can be identified by hybridization of candidate polynucleotides to known ceramide kinase polynucleotides under stringent conditions, as is known in the art. For example, using the following wash conditions—2× SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the ceramide kinase polynucleotides disclosed herein can be identified by making suitable probes or primers and screening cDNA expression libraries from other species, such as mice, monkeys, or yeast. Human variants of ceramide kinase polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human ceramide kinase polynucleotides or ceramide kinase polynucleotides of other species can therefore be identified, for example, by hybridizing a putative homologous ceramide kinase polynucleotide with a polynucleotide having a nucleotide sequence of SEQ ID NOS:1 and 9. The melting temperature of the test hybrid is compared with the melting temperature of a hybrid comprising ceramide kinase polynucleotides having perfectly complementary nucleotide sequences, and the number or percent of basepair mismatches within the test hybrid is calculated.

Nucleotide sequences which hybridize to ceramide kinase polynucleotides or their complements following stringent hybridization and/or wash conditions are also ceramide kinase polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a ceramide kinase polynucleotide having a coding sequence disclosed herein and a polynucleotide sequence which is at least about 50, 55, 60, 65, 70, preferably about 75, 90, 96, or 98% identical to that nucleotide sequence can be calculated, for example, using the equation of Bolton and McCarthy, *Proc. Natl. Acad. Sci. U.S.A.* 48, 1390 (1962):

$$T_m = 81.5° \text{ C.} - 16.6(\log_{10}[\text{Na}^+]) + 0.41(\% \text{ G+C}) - 0.63(\% \text{ formamide}) - 600/l,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A naturally occurring ceramide kinase polynucleotide can be isolated free of other cellular components such as membrane components, proteins, and lipids. Polynucleotides can be made by a cell and isolated using standard nucleic acid purification techniques, synthesized using an amplification technique, such as the polymerase chain reaction (PCR), or synthesized using an automatic synthesizer. Methods for isolating polynucleotides are routine and are known in the art. Any such technique for obtaining a polynucleotide can be used to obtain isolated ceramide kinase polynucleotides. For example, restriction enzymes and probes can be used to isolate polynucleotide fragments that comprise ceramide kinase protein nucleotide sequences. Isolated polynucleotides are in preparations that are free or at least 70, 80, or 90% free of other molecules.

Ceramide kinase protein cDNA molecules can be made with standard molecular biology techniques, using ceramide kinase mRNA as a template. Ceramide kinase cDNA molecules can thereafter be replicated using molecular biology techniques known in the art and disclosed in manuals such as Sambrook et al. (1989). An amplification technique, such as PCR, can be used to obtain additional copies of ceramide kinase polynucleotides, using either human genomic DNA or cDNA as a template.

Alternatively, synthetic chemistry techniques can be used to synthesize ceramide kinase polynucleotides. The degeneracy of the genetic code allows alternate nucleotide sequences to be synthesized which will encode a ceramide kinase polypeptide having, for example, the amino acid sequence shown in SEQ ID NOS:2, 10, and 11 or a biologically active variant of that sequence.

Obtaining Full-Length Polynucleotides

Various PCR-based methods can be used to extend the nucleic acid sequences encoding the disclosed portions of human ceramide kinase protein to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial. chromosome DNA (Lagerstrom et al., *PCR Methods Applic.* 1, 111–119, 1991). In this method, multiple restriction enzyme digestions and ligations are used to place an engineered double-stranded sequence into an unknown fragment of the DNA molecule before performing PCR.

Another method that can be used to retrieve unknown sequences is that of Parker et al., *Nucleic Acids Res.* 19, 3055–3060, 1991. Additionally, PCR, nested primers, and PROMOTERFINDER libraries (CLONTECH, Palo Alto, Calif.) can be used to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) that are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

Ceramnide kinase polypeptides can be obtained, for example, by purification from human cells, by expression of ceramide kinase polynucleotides, or by direct chemical synthesis.

Protein Purification

Figure 4:
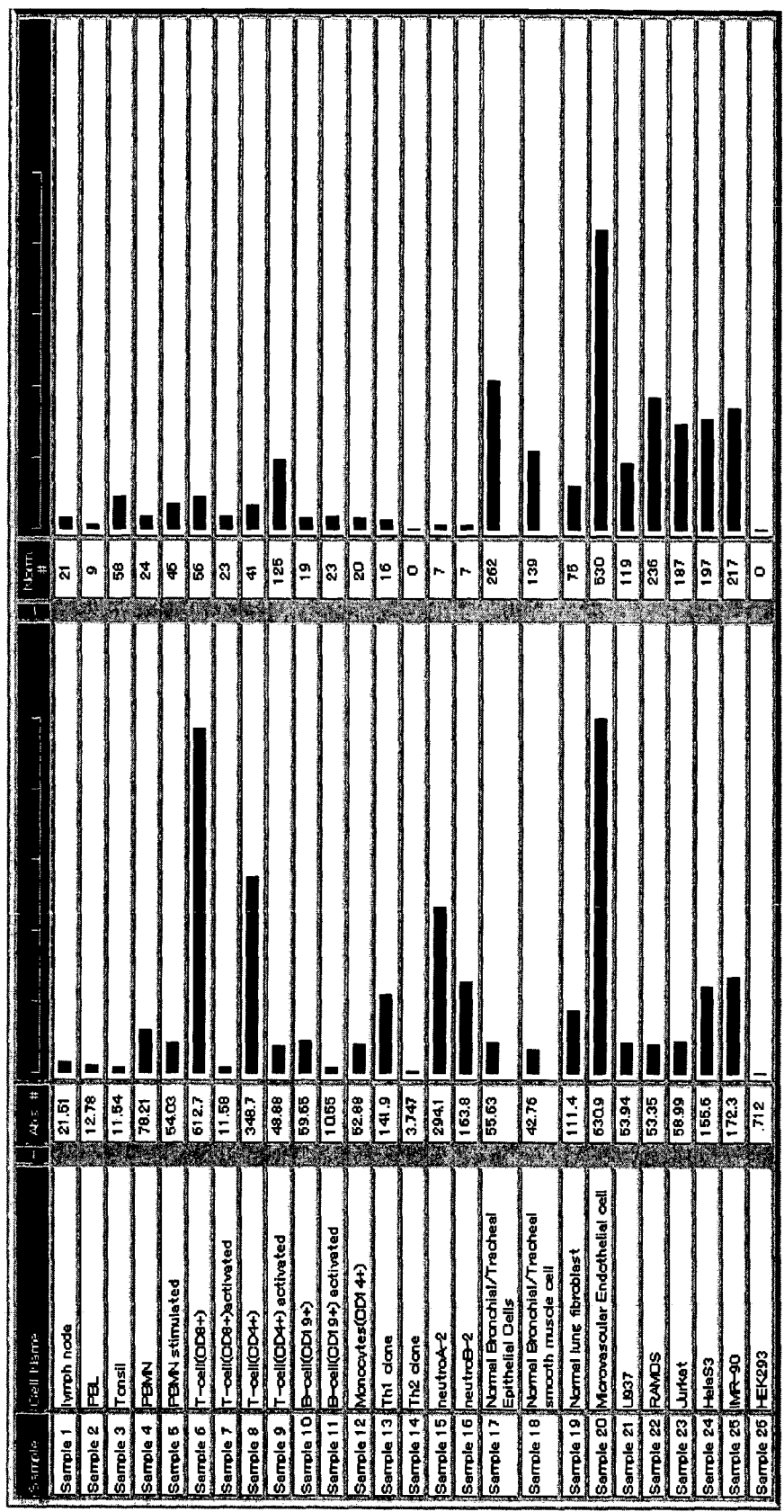
FIG. 4. Expression profiling of human ceramide kinase (SEQ ID NO:10), blood/lung screen.
Figure 5:
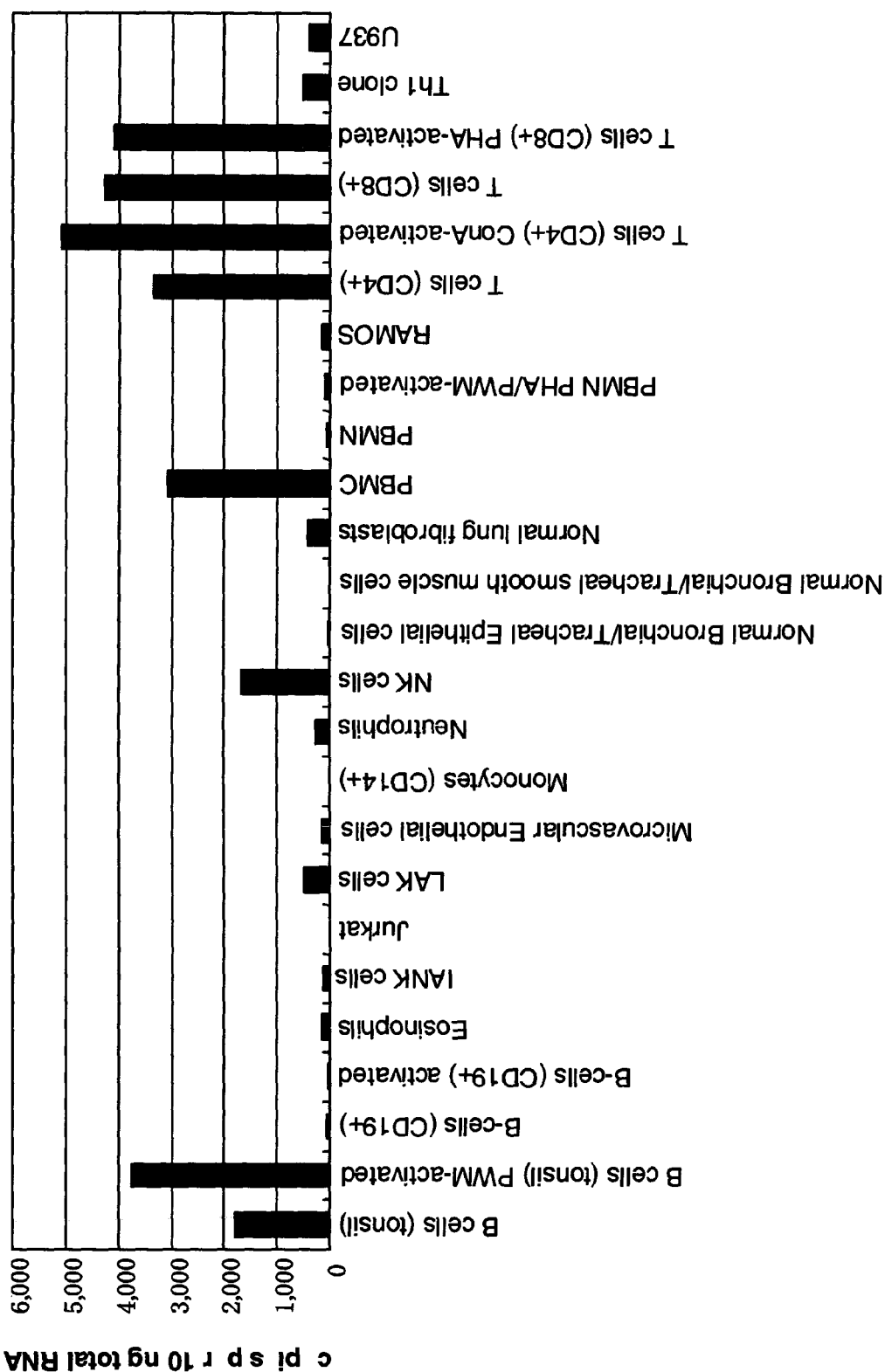
FIG. 5 Expression of human ceramide kinase gene transcripts in various human immune cells and primary cultured lung cell types.
Figure 6:
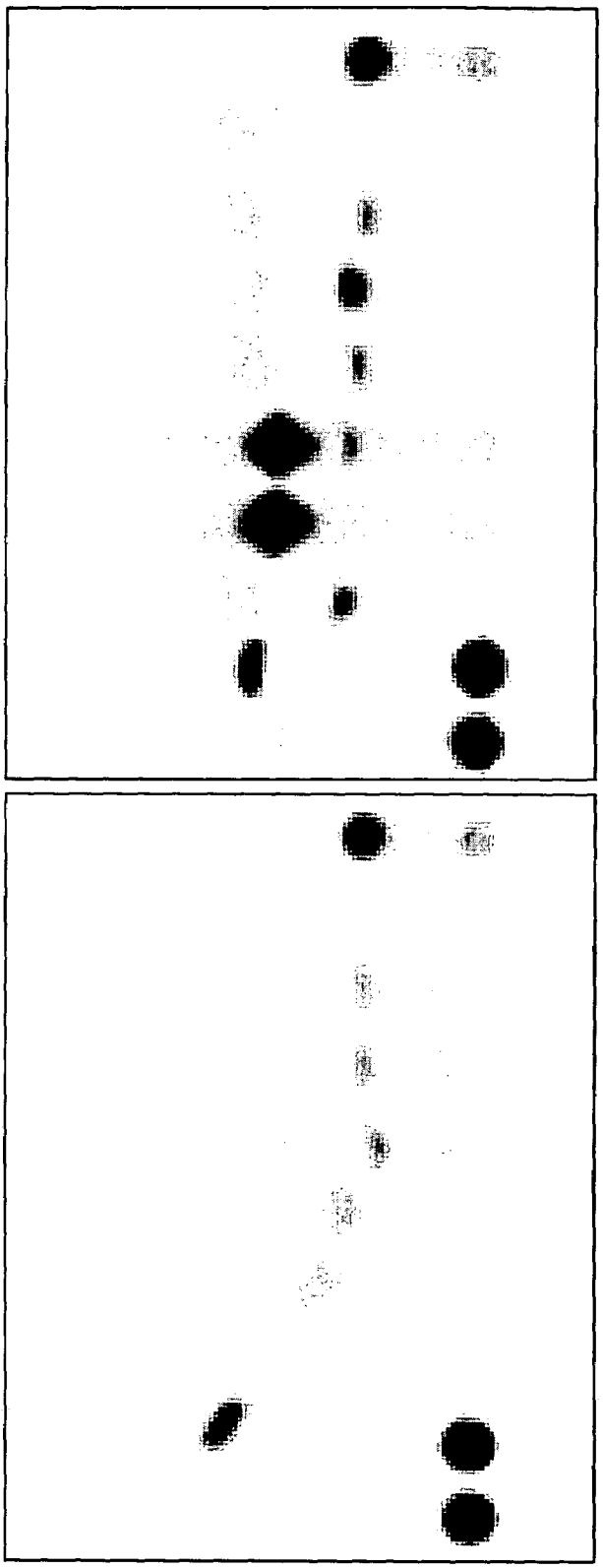
FIG. 6. Activity of human ceramide kinase expressed in HEK293 cells. Various sphingosine derivatives (C2 ceramide, C8 ceramide, sphingosine, sphinganine, and sulfatide), together with [$^{33}$P]ATP, were added to whole cell lysates of human ceramide kinase transfectants and non-transfectants, incubated for 2 hours at room temperature, extracted, and then subjected to thin layer chromatography. Migration standards of C2 ceramide-1-phosphate (lane 1), C8 ceramide-1-phosphate (lane 8), and sphingosine-1-phosphate (lane 10) were included as aids to identify the spots.
Figure 7:
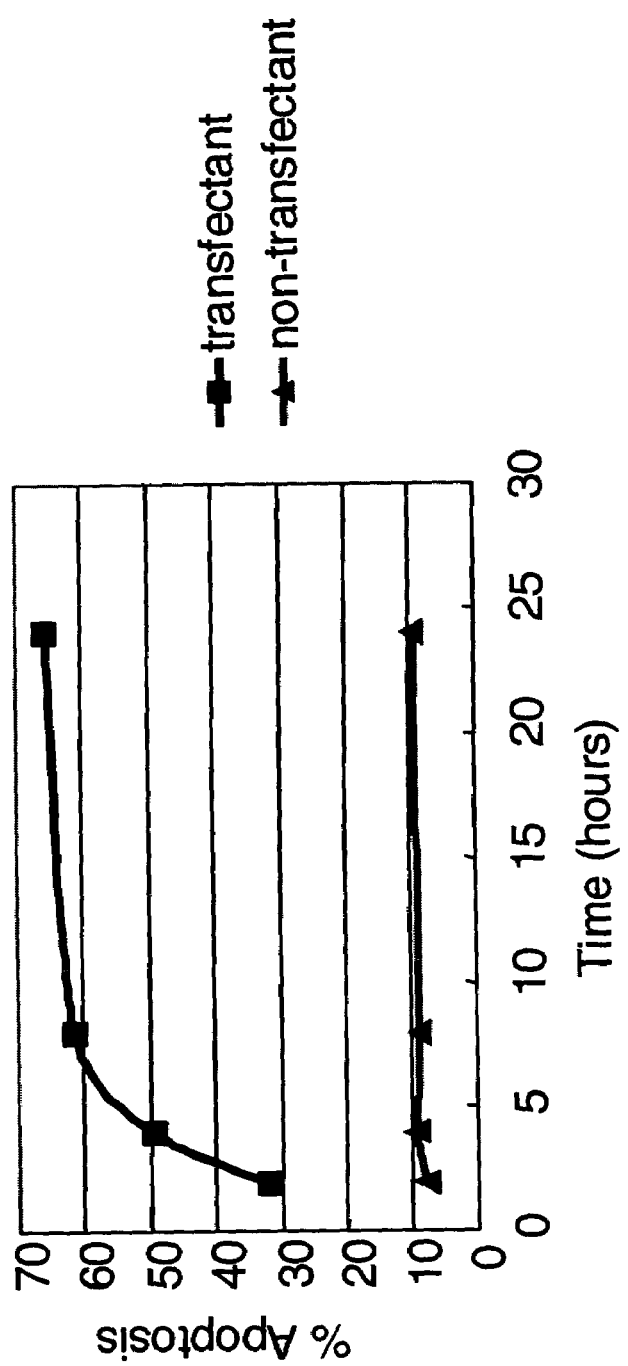
FIG. 7. Time course of apoptosis induction by C2 ceramide in human ceramide kinase stable transfectants and non-transfectants. C2 ceramide was added at the time point of 0 hours to cultures of transfectants and non-transfectants, and then at time points of 2, 4, 8, and 24 hours, percent of cells undergoing apoptosis was measured by the TUNEL assay.

Ceramide kinase polypeptides can be purified from human cells that expes the polypeptides (see FIGS. 3 and 4). A purified ceramide kinase polypeptide is separated from other compounds that normally associate with the ceramide kinase polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified ceramide kinase polypeptides is at least 80% pure; preferably, the preparations are 90%, 95%, or 99% pure. Purity of the preparations can be assessed by any means known in the art, such as SDS-polyacrylamide gel electrophoresis. Enzymatic activity of the purified preparations can be assayed, for example, as described above.

Expression of Polynucleotides

To express a human ceramide kinase polynucleotide, the polynucleotide can be inserted into an expression vector that contains the necessary elements for the transcription and translation of the inserted coding sequence. Methods yjay are well known to those skilled in the art can be used to construct expression vectors containing sequences encoding ceramide kinase polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a human ceramide kinase polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems. See WO 01/98340.

Host Cells

A host cell strain can be chosen for its ability to modulate the expression of the inserted sequences or to process the expressed ceramide kinase polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells that have specific cellular machinery and characteristic mechanisms for post-translational activities (e.g., CHO, HeLa, MDCK, HEK293, and WI38) are available from the American Type Culture Collection (ATCC; 10801 University Boulevard, Manassas, Va. 20110-2209) and can be chosen to ensure the correct modification and processing of the foreign protein. See WO 01/98340.

Detecting Expression of Polypeptides

Although the presence of marker gene expression suggests that the ceramide kinase polynucleotide is also present, its presence and expression may need to be confirmed. For example, if a sequence encoding a ceramide kinase polypeptide is inserted within a marker gene sequence, transformed cells containing sequences that encode a ceramide kinase polypeptide can be identified by the absence of marker gene function. Alternatively, a marker gene can be placed in tandem with a sequence encoding a ceramide kinase polypeptide under the control of a single promoter. Expression of the marker gene in response to induction or selection usually indicates expression of the ceramide kinase polynucleotide.

Alternatively, host cells which contain a ceramide kinase polynucleotide and which express a ceramide kinase polypeptide can be identified by a variety of procedures known to those of skill in the art. These procedures include, but are not limited to, DNA-DNA or DNA-RNA hybridizations and protein bioassay or immunoassay techniques that include membrane, solution, or chip-based technologies for the detection and/or quantification of nucleic acid or protein.

The presence of a polynucleotide sequence encoding a ceramide kinase polypeptide can be detected by DNA-DNA or DNA-RNA hybridization or amplification using probes or fragments or fragments of polynucleotides encoding a ceramide kinase polypeptide. Nucleic acid amplification-based assays involve the use of oligonucleotides selected from sequences encoding a ceramide kinase polypeptide to detect transformants that contain a ceramide kinase polynucleotide.

A variety of protocols for detecting and measuring the expression of a ceramide kinase polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a ceramide kinase polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding ceramide kinase polypeptides include oligolabeling, nick translation, end-labeling, or PCR amplification using a labeled nucleotide. Alternatively, sequences encoding a ceramide kinase polypeptide can be cloned into a vector for the production of an mRNA probe. Such vectors are known in the art, are commercially available, and can be used to synthesize RNA probes in vitro by addition of labeled nucleotides and an appropriate RNA polymerase, such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, fluorescent, chemiluminescent, or chromogenic agents, as well as substrates, cofactors, inhibitors, magnetic particles, and the like.

Expression and Purification of Polypeptides

Host cells transformed with nucleotide sequences encoding a ceramide kinase polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides that encode ceramide kinase polypeptides can be designed to contain signal sequences that direct secretion of ceramide kinase polypeptides through a prokaryotic or eukaryotic cell membrane.

Other constructions can be used to join a sequence encoding a cerarnide kinase polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor Xa or enterokinase (Invitrogen, San Diego, Calif.) between the purification domain and the ceramide kinase polypeptide can be used to facilitate purification. One such expression vector provides for expression of a fusion protein containing a ceramide kinase polypeptide and 6 histidine residues preceding a thioredoxin or an enterokinase cleavage site. The histidine residues facilitate purification on IMAC (immobilized metal ion affinity chromatography as described in Porath et al., *Prot. Exp. Purif.* 3, 263–281, 1992), while the enterokinase cleavage site provides a means for purifying the ceramide kinase polypeptide from the fusion protein. Vectors that contain fusion proteins are disclosed in Kroll et al., *DNA Cell Biol.* 12, 441–453, 1993).

Chemical Synthesis

Sequences encoding a ceramide kinase polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, a ceramide kinase polypeptide itself can be produced using chemical methods to synthesize its amino acid sequence. For example, ceramide kinase polypeptides can be produced by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Various fragments of ceramide kinase polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic ceramide kinase polypeptide can be confirmed by amino acid analysis or sequencing (e.g., the Edman degradation procedure; see Creighton, supra). Additionally, any portion of the amino acid sequence of the ceramide kinase polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce ceramide kinase polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life that is longer than that of a transcript generated from the naturally occurring sequence.

The nucleotide sequences disclosed herein can be engineered using methods generally known in the art to alter ceramide kinase polypeptide-encoding sequences for a variety of reasons, including modification of the cloning, processing, and/or expression of the gene. product. DNA shuffling by random fragmentation and PCR reassembly of gene. fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a human ceramide kinase polypeptide. "Antibody" as used herein includes intact immunoglobulin molecules, as well as fragments thereof, such as Fab, F(ab')$_2$, and Fv, that are capable of binding an epitope of a human ceramide kinase polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a human ceramide kinase polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody that specifically binds to the immunogen.

Typically, an antibody that specifically binds to a human ceramide kinase polypeptide provides a detection signal at least 5-, 10-, or 20-fold higher than a detection signal provided with other proteins when used in an immunochemical assay. Preferably, antibodies that specifically bind to ceramide kinase polypeptides do not detect other proteins in immunochemical assays and can immunoprecipitate a human ceramide kinase polypeptide from solution. See WO 01/98340.

Antisense Oligonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of ceramide kinase gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of ceramide kinase gene expression can be obtained by designing antisense oligonucleotides that will form duplexes to the control, 5', or regulatory regions of the ceramide kinase gene. Oligonucleotides derived from the transcription initiation site, e.g., between positions −10 and +10 from the start site, are preferred. Similarly, inhibition can be achieved using "triple helix" base-pairing methodology. Triple heix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes. See WO 01/98340.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a human ceramide kinase polynucleotide can be used to generate ribozymes that will specifically bind to mRNA transcribed from the ceramide kinase polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201). See WO 01/98340.

Differentially Expressed Genes

Described herein are methods for the identification of genes whose products interact with human ceramide kinase protein. Such genes may represent genes that are differentially expressed in disorders including, but not limited to, CNS disorders, cancer, particularly lymphocytic leukemias, allergic disease, inflammatory disease, autoimmune disease, and transplant rejection. Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human ceramide kinase gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

To identify differentially expressed genes total RNA or, preferably, mRNA is isolated from tissues of interest. For example, RNA samples are obtained from tissues of experimental subjects and from corresponding tissues of control subjects. Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., *Proc. Natl. Acad. Sci. U.S.A.* 85, 208–12, 1988), subtractive hybridization (Hedrick et al., *Nature* 308, 149–53; Lee et al., *Proc. Natl. Acad. Sci. U.S.A.* 88, 2825, 1984), and, preferably, differential display (Liang & Pardee, *Science* 257, 967–71, 1992; U.S. Pat. No. 5,262,311).

The differential expression information may itself suggest relevant methods -for the treatment of disorders involving the human ceramide kinase protein. For example, treatment may include a modulation of expression of the differentially expressed genes and/or the gene encoding the human ceramide kinase protein. The differential expression information may indicate whether the expression or activity of the differentially expressed gene or gene product or the human ceramide kinase gene or gene product are up-regulated or down-regulated.

Screening Methods

The invention provides methods for identifying modulators, i.e., candidate or test compounds which bind to ceramide kinase polypeptides or polynucleotides and/or have a stimulatory or inhibitory effect on, for example, expression or activity of the ceramide kinase polypeptide or polynucleotide. Decreased intracellular signaling is useful for preventing or suppressing malignant cells from metastasizing. Increased intracellular signaling may be desired, for example, in developmental disorders characterized by inappropriately low levels of intracellular signaling or in regeneration.

The invention provides assays for screening test compounds that bind to or modulate the activity of a ceramide kinase polypeptide or a ceramide kinase polynucleotide. A test compound preferably binds to a ceramide kinase polypeptide or polynucleotide. More preferably, a test compound decreases a ceramide kinase protein activity of a ceramide kinase polypeptide or expression of a ceramide kinase polynucleotide by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. Such compounds also may include, but are not limited to, other cellular proteins, peptides such as, for example, soluble peptides, including but not limited to, Ig-tailed fusion peptides, comprising extracellular portions of target gene product transmembrane receptors, and members of random peptide libraries (Lam, et al., *Nature* 354, 82–84, 1991; Houghten et al., *Nature* 354, 84–86, 1991), made of D- and/or L-configuration amino acids, phosphopeptides (including, but not limited to members of random or partially degenerate, directed phosphopeptide libraries (Songyang et al., *Cell* 72, 767–78, 1993), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), and small organic or inorganic molecules.

The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolutionr, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g. Houghten, *Biotechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad. Sci.* 97, 6378–6382, 1990; Felici, *J. Mol. Biol.* 222, 301–310, 1991; and Ladner, U.S. Pat. No. 5,223,409).

High Throughput Screening

Test compounds can be screened for the ability to bind to ceramide kinase polypeptides or polynucleotides or to affect ceramide kinase protein activity or ceramide kinase gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 μl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule that binds to and occupies the active site or the diacylglycerol kinase domain of the ceramide kinase polypeptide, such that normal biological activity is prevented. Examples of such small molecules include, but are not limited to, small peptides or peptide-like molecules. In binding assays, either the test compound or the ceramide kinase polypeptide can comprise a detectable label, such as a fluorescent, radioisotopic, chemiluminescent, or enzymatic label, such as horseradish peroxidase, alkaline phosphatase, or luciferase. Detection of a test compound that is bound to the ceramide kinase. polypeptide can then be accomplished, for example, by direct counting of radioemmission, by scintillation counting, or by determining conversion of an appropriate substrate to a detectable product.

Alternatively, binding of a test compound to a ceramide kinase polypeptide can be determined without labeling either of the interactants. For example, a microphysiometer can be used to detect binding of a test compound with a target polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a ceramide kinase polypeptide. (McConnell et al., *Science* 257, 1906–1912, 1992).

Determining the ability of a test compound to bind to a ceramide kinase polypeptide also can be accomplished using a technology such as real-time Bimolecular Interaction Analysis (BIA). Sjolander & Urbaniczky, *Anal. Chem.* 63, 2338–2345, 1991, and Szabo et al., *Curr. Opin. Struct. Biol.* 5, 699–705, 1995. BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a ceramide kinase polypeptide can be used as a "bait protein" in a two-hybrid assay or three-hybrid assay (see, e.g., U.S. Pat. No. 5,283, 317; Zervos et al., *Cell* 72, 223–232, 1993; Madura et al., *J. Biol. Chem.* 268, 12046–12054, 1993; Bartel et al., *Biotechniques* 14, 920–924, 1993; Iwabuchi et al., *Oncogene* 8, 1693–1696, 1993; and Brent WO94/10300), to identify other proteins which bind to or interact with the ceramide kinase polypeptide and modulate its activity.

The two-hybrid system is based on the modular nature of most transcription factors, which consist of separable DNA-binding and activation domains. Briefly, the assay utilizes two different DNA constructs. For example, in one construct a polynucleotide encoding a ceramide kinase polypeptide is fused to a polynucleotide encoding the DNA binding domain of a known transcription factor (e.g., GAL-4). In the other construct, a DNA sequence that encodes an unidentified protein ("prey" or "sample") is fused to a polynucleotide that codes for the activation domain of the known transcription factor. If the "bait" and the "prey" proteins are able to interact in vivo to form a protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein that interacts with the ceramide kinase polypeptide.

It may be desirable to immobilize either the ceramide kinase polypeptide (or polynucleotide) or the test compound to facilitate separation of bound from unbound forms of one or both of the interactants, as well as to accommodate automation of the assay. Thus, either the ceramide kinase polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the ceramide kinase polypeptide (or polynucleotide) or test compound to a solid support, including use of covalent and non-covalent linkages, passive absorption, or pairs of binding moieties attached respectively to the polypeptide or test compound and the solid snuppsort. Test compounds are preferably bound to the solid support in an array, so that the location of individual test compounds can be tracked. Binding of a test compound to a ceramide kinase polypeptide (or polynucleotide) can be accomplished in any vessel suitable for containing the reactants. Examples of such vessels include microtiter plates, test tubes, and microcentrifuge tubes.

In one embodiment, a ceramide kinase polypeptide is a fusion protein comprising a domain that allows the ceramide kinase polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed ceramide kinase polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing polypeptides or polynucleotides on a solid support also can be used in the screening assays of the invention. For example, either a ceramide kinase polypeptide (or polynucleotide) or a test compound can be immobilized utilizing conjugation of biotin and streptavidin. Biotinylated ceramide kinase polypeptides or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a ceramide kinase polypeptide polynucleotides, or a test compound, but which do not interfere with a desired binding site, such as the active site or a fibronectin domain of the ceramide kinase polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the ceramide kinase polypeptide (or polynucleotides) or test compound, enzyme-linked assays which rely on detecting a ceramide kinase protein activity of the ceramide kinase polypeptide, and SDS gel electrophoresis under non-reducing conditions.

Screening for test compounds which bind to a ceramide kinase polypeptide or polynucleotide also can be carried out in an intact cell. Any cell which comprises a ceramide kinase polynucleotide or polypeptide can be used in a cell-based assay system. A ceramide kinase polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA-468, SK-BR3, and BT-474, the A549 lung cancer cell line, and the H392 glioblastoma cell line, can be used. An intact cell is contacted with a test compound. Binding of the test compound to a ceramide kinase polypeptide or polynucleotide is determined as described above, after lysing the cell to release the ceramide kinase polypeptide-test compound complex.

Enzyme Assays

Test compounds can be tested for the ability to increase or decrease a ceramide kinase activity of a ceramide kinase polypeptide. Ceramide kinase activity can be measured; for example, as described in J Biol Chem. Nov. 5, 1990; 265(31):18803–8. Ceramide kinase activity can be measured after contacting either a purified ceramide kinase polypeptide, a cell extract, or an intact cell with a test compound. A test compound that decreases ceramide kinase activity by at least about 10, preferably about 50, more preferably about 75, 90, or 100% is identified as a potential therapeutic agent for decreasing intracellular signaling. A test compound which increases ceramide kinase protein activity by at least about 10, preferably about 50, more preferably about 75, 90, or 100% is identified as a potential therapeutic agent for increasing intracellular signaling.

Gene Expression

In another embodiment, test compounds that increase or decrease ceramide kinase gene expression are identified. A ceramide kinase polynucleotide is contacted with a test compound, and the expression of an RNA or polypeptide product of the ceramide kinase polynucleotide is determined. The level of expression of ceramide kinase mRNA or polypeptide in the presence of the test compound is compared to the level of expression of ceramide kinase mRNA or polypeptide in the absence of the test compound. The test compound can then be identified as a modulator of expression based on this comparison. For example, when expression of ceramide kinase mRNA or polypeptide is greater in the presence of the test compound than in its absence, the test compound is identified as a stimulator or enhancer of ceramide kinase mRNA or polypeptide is less expression. Alternatively, when expression of the mRNA or protein is less in the presence of the test compound than in its absence, the test compound is identified as an inhibitor of ceramide kinase mRNA or polypeptide expression.

The level of ceramide kinase protein mRNA or polypeptide expression in the cells can be determined by methods well known in the art for detecting mRNA or protein. Either qualitative or quantitative methods can be used. The presence of polypeptide products of a ceramide kinase polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a cerarmide kinase polypeptide.

Such screening can be carried out either in a cell-free assay system or in an intact cell. Any cell that expresses a ceramide kinase polynucleotide can be used in a cell-based assay system. The ceramide kinase polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA-468, SK-BR3, and BT-474, the A549 lung cancer cell line, and the H392 glioblastoma cell line, can be used.

Pharmaceutical Compositions

The invention also provides pharmaceutical compositions that can be administered to a patient to achieve a therapeutic effect. Pharmaceutical compositions of the invention can comprise a ceramide kinase polypeptide, ceramide kinase polynucleotide, antibodies which specifically bind to a ceramide kinase polypeptide, or mimetics, agonists, antagonists, or inhibitors of a ceramide kinase polypeptide. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, ric, sulfric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

The consequences of direct phosphorylation of ceramide to produce ceramide-1-phosphate are less well understood. Most studies on the activity of ceramide-1-phosphate have found it to be an inducer of cell proliferation. Thus it would be reasonable to assume that the role of ceramide-1-phosphate is similar to that of sphingosine-1-phosphate; that is, counteracting the apoptosis-promoting effects of ceramide. The phosphorylation of ceramide to ceramide-1-phosphate may additionally serve to dampen ceramide signaling by disabling the molecule and removing it from the signaling cascade.

According to this theory, overexpression of human ceramide kinase, which phosphorylates ceramide to ceramide-1-phosphate, should make cells more resistant to apdptosis. Contrary to this, however, HEK293 cells that stably express human ceramide kinase are exquisitely susceptible to apoptosis induced by exogenously added C2 ceramide. As shown in FIG. 3, non-transfected HEK293 cells, which express little or no endogenous human ceramide kinase, are highly resistant to C2 ceramide-induced apoptosis, with less than 10% of cells undergoing apoptosis during a 24 hour treatment period. Human ceramide kinase-expressing cells on the other hand show greater than 60% of cells undergoing apoptosis after 8 hours treatment, indicating that human ceramide kinase promotes, rather than prevents, ceramide-mediated apoptosis.

Figure 8:
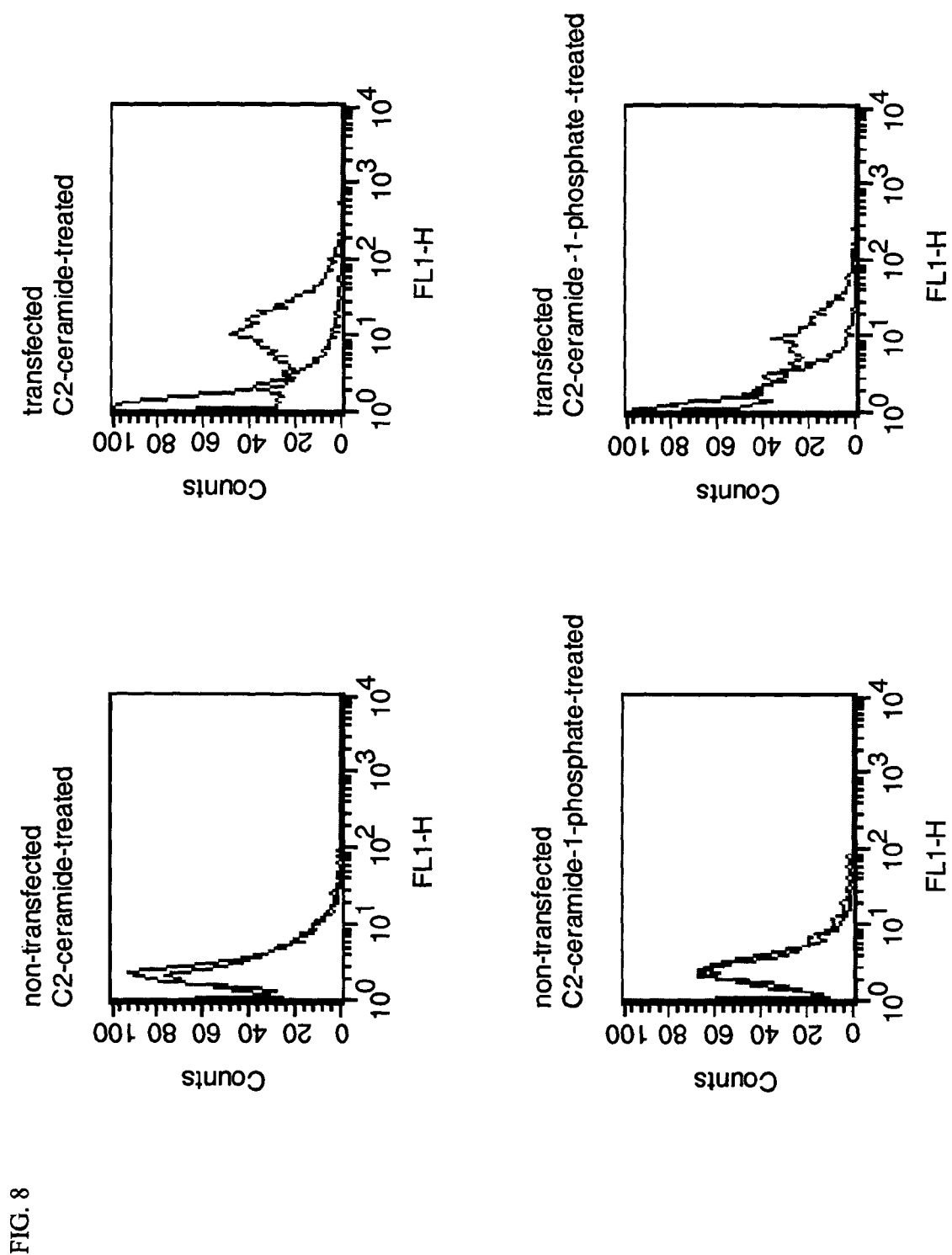
FIG. 8. Induction of apoptosis in human ceramide kinase transfected and non-transfectants by C2 ceramide and C2 ceramide-1-phosphate. Cells were treated with C2 ceramide or C2 ceramide-1-phosphate for 24 hours, after which apoptosis was detected by flow cytometry using a TUNEL assay. Fluorescence intensity of untreated cells are shown as a black curve while that of treated cells is shown as a gray curve. A shift of the curve to the right indicates incorporation of fluorescein-labeled dUTP into the cleaved DNA characteristic of apoptosis.

The contribution of human ceramide kinase to the cascade of signals that ultimately result in apoptosis does not appear to be solely due to its ability to generate ceramide-1-phosphate from ceramide. As shown in FIG. 8, the addition of C2 ceramide-1-phosphate to human ceramide kinase-expressing cells also induces apoptosis while having no significant effect on non-transfected cells. Therefore, human ceramide kinase can be considered to be a promoter of apoptosis not only by generating molecules of the apoptosis signaling cascade, but possibly also by localizing the molecules to sites or organelles where they may be the most effective, or by facilitating their transport across biological membranes.

Expression profiling of human ceramide kinase showed that it is expressed highly in lymphocytes, including resting and mitogenically activated $CD4^+$ T cells, $CD8^+$ T cells, tonsil-derived B cells, and natural killer cells. Thus, human ceramide kinase could be a potential target for treating allergic disease, inflammatory disease, autoimmune disease, transplant rejection, and lymphocytic leukemias, and could be a useful target of vaccination enhancing adjuvants. Human ceramide kinase of the invention also can be used to treat neurodegenerative diseases, including CNS disorders, and cancers.

Neurodegenerative Diseases

Ceramide kinase provides a therapeutic target for upregulating SPP to prevent apoptosis, in particular for treating or preventing CNS disorders such as brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, and Korsakoff's psychosis also can be treated. Similarly, it is possible to treat cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities, by regulating the activity of human ceramide kinase protein.

Cancer

Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

Autoimmune Disease

The principal physiologic function of the immune system is the elimination of infectious organisms. The effector mechanisms that are responsible for protective immunity are also capable of injuring host tissues. In some situations, specific immune responses have little or no protective value, and the harmful consequences become dominant. The best example of this is autoimmune disease caused by pathologic immune responses against self-antigens. (See U.S. Pat. No. 6,098,631).

Potentially harmful immune reactions may be prevented either by functionally inactivating or killing the responding lymphocytes. The primary cytolytic mechanism involved in controlling lymphocyte responses is the Fas-mediated apoptotic pathway. Using this pathway, the immune system actively eliminates potentially harmful cells so that the host may survive. See A. Abbas, "Die and Let Live: Eliminating Dangerous Lymphocytes," Cell 84:655 (1996). Abnormalities in Fas-mediated cell death pathways may result in autoimmunity even in situations in which Fas and Fas Ligand are themselves normal. For example, where apoptosis is inhibited and a proliferation pathway is stimulated, activated lymphocytes may escape elimination and cause disease.

Established treatments of autoimmune disease are designed to inhibit either final common pathways of inflammation or immunological mediators. Both approaches are non-specific and, therefore, are associated with severe side effects, such as musculoskeletal, metabolic, neurologic and connective tissue side effects, immunosuppression, bone marrow and gastrointestinal toxicity, liver damage, lung disease, hypersensitivity reactions, deafness, renal toxicity, mucocutaneous toxicity. See, R. Million et al., *Lancet* 1:812 (1984), J. A. Engelbrecht et al., *Arthritis and Rheumatism* 26:1275 (1983), G. W. Cannon et al., *Arthritis and Rheumatism* 26:1269 (1983), Simon and Mills, "Nonsteroidal Antiinflammatory Drugs," N. Eng. J. Med. 302:1179 (1980), Katz et al., *Ann. Int. Med.* 101:176 (1984), W. F. Kean et al., *Arthritis and Rheumatism* 23:158 (1980).

Thus, current therapies for autoimmune diseases are associated with high incidence of serious side effects. Furthermore, although some medications may offer symptomatic relief, in many cases, they do not significantly modify the progression of symptoms such as joint destruction. What is needed is an effective therapeutic approach with lower toxicity such that the treatment is better tolerated and more appropriate for the treatment of autoimmune diseases.

Allergies

Regulation of ceramide kinase protein activity may provide a method of treating allergies. The first step in the pathogenesis of an allergic response is the production of immunoglobulin E (IgE) antibody in response to an allergen. Upon exposure to allergens the B cells of responsive individuals secrete IgE molecules specific to the allergen. IgE molecules bind to the high affinity IgE receptor (FcRI) present on mast cells and basophils. (See U.S. Pat. No. 5,977,072).

IgE binding activates the release of a variety of vasoactive mediators that promote allergic and inflammatory responses. Activation occurs whenever 2 or more FcRIs are crosslinked via bound IgE molecules that in turn form an aggregate with an allergen molecule. Such aggregation initiates a biochemical cascade that releases histamine and proteases from cytoplasmic granules and leads to the synthesis of prostaglandins, leukotrienes, cytokines and other effectors of the hypersensitivity response.

Mast cells and basophils accumulate at sites of inflammation and, upon activation, secrete hematopoietic growth factors such as granulocyte/macrophage colony-stimulating factor, interleukin-3, and interleukin-6. These factors propagate the inflammatory response by recruiting, priming, and activating inflammatory cells such as neutrophils, macrophages and eosinophils. The activated cells accumulate in areas of ongoing inflammation, tumor invasion, angiogenesis, fibrosis, and thrombosis. The IgE-dependent activation of cells via FcRI results in an inflammatory response directed towards local tissue defense, tissue maintenance and remodeling, and immunoregulation (Gagari, E. et al (1997) Blood 89:2654–2663).

IgE binding to the FcRI activates kinases that are bound to the receptor under resting conditions. When the receptor is phosphorylated, it recruits and activates signaling molecules, such as syk, which activate downstream effector molecules. The phosphorylated receptor activates sphingosine kinase, which contributes to calcium mobilization in mast cells. Other early events induced by FcRI aggregation are the activation of the tyrosine kinases, Lyn and Syk, and the tyrosine phosphorylation of cytoplasmic molecules including phospholipase C. Phosphorylated phospholipase C hydrolyses phosphatidylinositol 4,5-bisphosphate and liberates inositol 1,4,5-trisphosphate and diacylglycerol. The latter mobilizes Ca2+ from intracellular and extracellular sources and activates protein kinase C (Paolini, R. et al. (1991) Nature 353: 855–858; and Beaven, M. A. and Baumgartner, R. A. (1996) Curr. Opin. Immunol. 8:766–772).

The invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a polypeptide-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects ceramide kinase protein activity can be administered to a human cell, either in vitro or in vivo, to reduce ceramide kinase protein activity. The reagent preferably binds to an expression product of a human ceramide kinase gene. If the expression product is a polypeptide, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung or liver.

A liposome useful in the present invention comprises a lipid composition that is capable of fusing with the plasma membrane of the targeted cell to deliver its contents to the cell. Preferably, the transfection efficiency of a liposome is about 0.5 μg of DNA per 16 nmole of liposome delivered to about $10^6$ cells, more preferably about 1.0 μg of DNA per 16 nmol of liposome delivered to about $10^6$ cells, and even more preferably about 2.0 μg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art.

More preferred liposomes include liposomes having a polycationic lipid composition and/or liposomes having a cholesterol backbone conjugated to polyethylene glycol. Optionally, a liposome comprises a compound capable of targeting the liposome to a tumor cell, such as a tumor cell ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 µg to about 10 µg of polynucleotideis-combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Determination of a Therapeutically Effective Dose

The determination of a therapeutically effective dose is well within the capability of those skilled in the art. A therapeutically effective dose refers to that amount of active ingredient that increases or decreases intracellular signaling relative to that which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject what requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides that express antisense oligonucleotides or ribozymes can be introduced into cells by a variety of methods, as described above.

Preferably, a reagent reduces expression of a ceramide kinase polynucleotide or activity of a ceramide kinase polypeptide by at least about 10, preferably about 50, more preferably about 75, 90, or 100% relative to the absence of the reagent. The effectiveness of the mechanism chosen to decrease the level of expression of a ceramide kinase polynucleotide or the activity of a ceramide kinase polypeptide can be assessed using methods well known in the art, such as hybridization of nucleotide probes to ceramide kinase protein-specific mRNA, quantitative RT-PCR, immunologic detectioni of a ceramide kinase polypeptide, or measurement of ceramide kinase protein activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

The above disclosure generally describes the present invention, and all patents and patent applications cited in this disclosure are expressly incorporated herein. A more complete understanding can be obtained by reference to the following specific examples which are provided for purposes of illustration only and are not intended to limit the scope of the invention.

EXAMPLE 1

Identification of a Test Compound that Binds to a Ceramide Kinase Polypeptide

Purified ceramide kinase polypeptides comprising a glutathione-S-transferase protein are absorbed onto glutathione-derivatized wells of 96-well microfiter plates are contacted with test compounds from a small molecule library at pH 7.0 in a physiological buffer solution. Ceramide kinase polypeptides comprise the amino acid sequence shown in SEQ ID NOS:2, 10, and 11. The test compounds comprise a fluorescent tag. The samples are incubated for 5 minutes to one hour. Control samples are incubated in the absence of a test compound.

The buffer solution containing the test compounds is washed from the wells. Binding of a test compound to a ceramide kinase polypeptide is detected by fluorescence measurements of the contents of the wells. A test compound that increases the fluorescence in a well by at least 15% relative to fluorescence of a well in which a test compound was not incubated is identified as a compound that binds to a ceramide kinase polypeptide.

EXAMPLE 2

Identification of a Test Compound which Decreases Ceramide Kinase Protein Activity A test compound is administered to a primary culture of MC3T3-E1 osteoblast cells and incubated at 37° C. for 10 to 45 minutes. A culture of the same type of cells incubated for the same time without the test compound provides a negative control.

RNA is isolated from the two cultures as described in Chirgwin et al., *Biochem.* 18, 5294–99, 1979). Northern blots are prepared using 20 to 30 µg total RNA and hybridized with a $^{32}$P-labeled ceramide kinase protein-specific probe at 65° C. in Express-hyb (CLONTECH). The probe comprises at least 11 contiguous nucleotides selected from the complement of SEQ ID NOS:1 and 9. A test compound that decreases the ceramide kinase protein-specific signal relative to the signal obtained in the absence of the test compound is identified as an inhibitor of ceramide kinase gene expression.

EXAMPLE 3

Treatment of a Tumor with a Reagent that Specifically Binds to a Ceramide Kinase Gene Product Synthesis of antisense ceramide kinase protein oligonucleotides comprising at least 11 contiguous nucleotides selected from the complement of SEQ ID NOS:1 and 9 is performed on a Pharmacia Gene Assembler series synthesizer using the phosphoroamidite procedure (Uhlmann et al., *Chem. Rev.* 90, 534–83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the Limulus Amebocyte Assay (Bang, *Biol. Bull.* (Woods Hole, Mass.) 105, 361–362, 1953).

A composition containing the antisense oligonucleotides at a concentration of 0.1–100 µM is administered directly into the tumor. Tumor size is monitored over a period of days or weeks. Additional doses of the antisense oligonucleotides can be given during that time. Tumor growth is suppressed due to decreased ceramide kinase protein activity.

EXAMPLE 4

Treatment of a Rheumatoid Arthritis with a Reagent that Specifically Binds to a Ceramide Kinase Gene Product Synthesis of antisense ceramide kinase protein oligonucleotides comprising at least 11 contiguous nucleotides selected from the complement of SEQ ID NOS:1 and 9 is performed on a Pharmacia Gene Assembler series synthesizer using the phosphoroamidite procedure (Uhlmann et al., *Chem. Rev.* 90, 534–83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the Limulus Amebocyte Assay (Bang, *Biol. Bull.* (Woods Hole, Mass.) 105, 361–362, 1953).

An aqueous composition containing the antisense oligonucleotides at a concentration of 0.1–100 µM is administered to the patient using a needle.

Severity of rheumatoid arthritis atherosclerosis is monitored over a period of days or weeks by removing synovial fluid from the knee joint, isolating synovial T cells, and determining whether the T cells are resistant to Fas-mediated DNA fragmentation. Briefly, the T cells were lysed in TE buffer containing 0.2% Triton X-100, pH 8. Fragmented DNA was separated from intact chromatin by microfuging for 20 min, 14,000 rpm at 4° C. The resulting supernatant is treated with 1 mg/ml of proteinase K at 37° C. overnight, then extracted with phenol/chloroform/isoamyl alcohol (25:24:1) three times. DNA is precipitated by addition of three volumes of absolute ethanol, in the presence of 0.3 M sodium acetate, pH 5.2, incubated overnight at −20° C. and then pelleted by centrifugation at 14,000 rpm at 4° C. for 20 min. The pellet is washed twice with 75% ethanol and dissolved in 30 µl of TE containing 10 µg/ml of RNase overnight at 37° C. DNA samples are separated by electrophoresis on 1.8% agarose gel in the presence of ethidium bromide. Additional injections of the antisense oligonucleotides can be given during that time. Rheumatoid arthritis is suppressed due to decreased ceramide kinase protein activity.

EXAMPLE 5

Proliferation Inhibition Assay: Antisense Oligonucleotides Suppress the Growth of Cancer Cell Lines The cell line used for testing is the human colon cancer cell line HCT116. Cells are cultured in RPMI-1640 with 10–15% fetal calf serum at a concentration of 10,000 cells per milliliter in a volume of 0.5 ml and kept at 37° C. in a 95% air/5% $CO_2$ atmosphere.

Phosphorothioate oligoribonucleotides are synthesized on an Applied Biosystems Model 380B DNA synthesizer using phosphoroamidite chemistry. A sequence of 24 bases is used as the test oligonucleotide: (1) 5'-TGG TTT CGT AAA TGA CCA TAA ATA-3' (SEQ ID NO:14, complementary to the nucleotides at position 1 to 24 of SEQ ID NOS:2, 10, and 11). As a control, another (random) sequence is used: 5'-TCA ACT GAC TAG ATG TAC ATG GAC-3' (SEQ ID NO:15). Following assembly and deprotection, oligonucleotides are ethanol-precipitated twice, dried, and suspended in phosphate buffered saline at the desired concentration. Purity of the oligonucleotides is tested by capillary gel electrophoresis and ion exchange HPLC. The purified oligonucleotides are added to the culture medium at a concentration of 10 µM once per day for seven days.

The addition of the test oligonucleotide for seven days results in significantly reduced expression of human ceramide kinase protein as determined by Western blotting. This effect is not observed with the control oligonucleotide. After 3 to 7 days, the number of cells in the cultures is counted using an automatic cell counter. The number of cells in cultures treated with the test oligonucleotide (expressed as 100%) is compared with the number of cells in cultures treated with the control oligonucleotide. The number of cells in cultures treated with the test oligonucleotide is not more than 30% of control, indicating that the inhibition of human ceramide kinase protein has an anti-proliferative effect on cancer cells.

EXAMPLE 6

In Vivo Testing of Compounds/Target Validation

Acute Mechanistic Assays

Reduction in Mitogenic Plasma Hormone Levels. This non-tumor assay measures the ability of a compound to reduce either the endogenous level of a circulating hormone or the level of hormone produced in response to a biologic stimulus. Rodents are administered test compound (p.o., i.p., i.v., i.m., or s.c.). At a predetermined time after administration of test compound, blood plasma is collected. Plasma is assayed for levels of the hormone of interest. If the normal circulating levels of the hormone are too low and/or variable to provide consistent results, the level of the hormone may be elevated by a pre-treatment with a biologic stimulus (i.e., LHRH may be injected i.m. into mice at a dosage of 30 ng/mouse to induce a burst of testosterone synthesis). The timing of plasma collection would be adjusted to coincide with the peak of the induced hormone response. Compound effects are compared to a vehicle-treated control group. An F-test is preformed to determine if the variance is equal or unequal followed by a Student's t-test. Significance is p value≦0.05 compared to the vehicle control group.

Hollow Fiber Mechanism of Action Assay. Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol, these may include assays for gene expression (bDNA, PCR, or Taqman), or a specific biochemical activity (i.e., cAMP levels. Results are analyzed by Student's t-test or Rank Sum test after the variance between groups is compared by an F-test, with significance at p≦0.05 as compared to the vehicle control group.

Subacute Functional In Vivo Assays

Reduction in Mass of Hormone Dependent Tissues. This is another non-tumor assay that measures the ability of a compound to reduce the mass of a hormone dependent tissue (i.e., seminal vesicles in males and uteri in females). Rodents are administered test compound (p.o., i.p., i.v., i.m., or s.c.) according to a predetermined schedule and for a predetermined duration (i.e., 1 week). At termination of the study, animals are weighed, the target organ is excised, any fluid is expressed, and the weight of the organ is recorded. Blood plasma may also be collected. Plasma may be assayed for levels of a hormone of interest or for levels of test agent. Organ weights may be directly compared or they may be normalized for the body weight of the animal. Compound effects. are compared to a vehicle-treated control group. An F-test is preformed to determine if the variance is equal or unequal followed by a Student's t-test. Significance is p value≦0.05 compared to the vehicle control group.

Hollow Fiber Proliferation Assay. Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol. Cell proliferation is determined by measuring a marker of cell number (i.e., MTT or LDH). The cell number and change in cell number from the starting inoculum are analyzed by Student's t-test or Rank Sum test after the variance between groups is compared by an F-test, with significance at p≦0.05 as compared to the vehicle control group.

Anti-angiogenesis Models

Corneal Angiogenesis. Hydron pellets with or without growth factors or cells are implanted into a micropocket surgically created in the rodent cornea. Compound administration may be systemic or local (compound mixed with growth factors in the hydron pellet). Corneas are harvested at 7 days post implantation immediately following intracardiac infusion of colloidal carbon and are fixed in 10% formalin. Readout is qualitative scoring and/or image analysis. Qualitative scores are compared by Rank-Sum test. Image analysis data is evaluated by measuring the area of neovascularization (in pixels) and group averages are compared by Student's t-test (2 tail). Significance is p≦0.05 as compared to the growth factor or cells only group.

Matrigel Angiogenesis. Matrigel, containing cells or growth factors, is injected subcutaneously. Compounds are administered p.o., i.p., i.v., i.m., or s.c. Matrigel plugs are harvested at predetermined time point(s) and prepared for readout. Readout is an ELISA-based assay for hemoglobin concentration and/or histological examination (i.e. vessel count, special staining for endothelial surface markers: CD31, factor-8). Readouts are analyzed by Student's t-test, after the variance between groups is compared by an F-test, with significance determined at p≦0.05 as compared to the vehicle control group.

Primary Antitumor Efficacy

Early Therapy Models

Subcutaneous Tumor. Tumor cells or fragments are implanted subcutaneously on Day 0. Vehicle and/or compounds are administered p.o., i.p., i.v., i.m., or s.c. according to a predetermined schedule starting at a time, usually on Day 1, prior to the ability to measure the tumor burden. Body weights and tumor measurements are recorded 2–3 times weekly. Mean net body and tumor weights are calculated for each data collection day. Anti-tumor efficacy may be initially determined by comparing the size of treated (T) and control (C) tumors on a given day by a Student's t-test, after the variance between groups is compared by an F-test, with significance determined at $p \leq 0.05$. The experiment may also be continued past the end of dosing in which case tumor measurements would continue to be recorded to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is $p \leq 0.05$.

Intraperitoneal/Intracranial Tumor Models. Tumor cells are injected intraperitoneally or intracranially on Day 0. Compounds are administered p.o., i.p., i.v., i.m., or s.c. according to a predetermined schedule starting on Day 1. Observations of morbidity and/or mortality are recorded twice daily. Body weights are measured and recorded twice weekly. Morbidity/mortality data is expressed in terms of the median time of survival and the number of long-term survivors is indicated separately. Survival times are used to generate Kaplan-Meier curves. Significance is $p \leq 0.05$ by a log-rank test compared to the control group in the experiment.

Established Disease Model

Tumor cells or fragments are implanted subcutaneously and grown to the desired size for treatment to begin. Once at the predetermined size range, mice are randomized into treatment groups. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group. Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group.

Orthotopic Disease Models

Mammary Fat Pad Assay. Tumor cells or fragments, of mammary adenocarcinomaa origin, are implanted directly into a surgically exposed and reflected mammary fat pad in rodents. The fat pad is placed back in its original position and the surgical site; is closed. Hormones may also be administered to the rodents to support the growth of the tumors. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group.

Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group. In addition, this model provides an opportunity to increase the rate of spontaneous metastasis of this type of tumor. Metastasis can be assessed at termination of the study by counting the number of visible foci per target organ, or measuring the target organ weight. The means of these endpoints are compared by Student's t-test after conducting an F-test, with significance determined at $p \leq 0.05$ compared to the control group in the experiment.

Intraprostatic Assay. Tumor cells or fragments, of prostatic adenocarcinoma origin, are implanted directly into a surgically exposed dorsal lobe of the prostate in rodents. The prostate is externalized through an abdominal incision so that the tumor can be implanted specifically in the dorsal lobe while verifying that the implant does not enter the seminal vesicles. The successfully inoculated prostate is replaced in the abdomen and the incisions through the abdomen and skin are closed. Hormones may also be administered to the rodents to support the growth of the tumors. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the lungs), or measuring the target organ weight (i.e., the regional lymph nodes). The means of these endpoints are compared by Student's t-test after conducting an F-test, with significance determined at $p \leq 0.05$ compared to the control group in the experiment.

Intrabronchial Assay. Tumor cells of pulmonary origin may be implanted intrabronchially by making an incision through the skin and exposing the trachea. The trachea is pierced with the beveled end of a 25 gauge needle and the tumor cells are inoculated into the main bronchus using a flat-ended 27 gauge needle with a 90° bend. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the contralateral lung), or measuring the target organ weight. The means of these endpoints are compared by Student's t-test after conducting an F-test, with significance determined at $p \leq 0.05$ compared to the control group in the experiment.

Intracecal Assay. Tumor cells of gastrointestinal origin may be implanted intracecally by making an abdominal incision through the skin and externalizing the intestine. Tumor cells are inoculated into the cecal wall without penetrating the lumen of the intestine using a 27 or 30 gauge needle. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the liver), or measuring the target organ weight. The means of these endpoints are compared by Student's t-test after conducting an F-test, with significance determined at $p \leq 0.05$ compared to the control group in the experiment.

Secondary (Metastatic) Antitumor Efficacy

Spontaneous Metastasis

Tumor cells are inoculated s.c. and the tumors allowed to grow to a predetermined range for spontaneous metastasis studies to the lung or liver. These primary tumors are then excised. Compounds are administered p.o., i.p., i.v., i.m., or s.c. according to a predetermined schedule which may include the period leading up to the excision of the primary tumor to evaluate therapies directed at inhibiting the early stages of tumor metastasis. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance determined at $p \leq 0.05$ compared to the control group in the experiment for both of these endpoints.

Forced Metastasis

Tumor cells are injected into the tail vein, portal vein, or the left ventricle of the heart in experimental (forced) lung, liver, and bone metastasis studies, respectively. Compounds are administered p.o., i.p., i.v., i.m., or s.c. according to a predetermined schedule. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's.t-test after conducting an F-test, with significance at $p \leq 0.05$ compared to the vehicle control group in the experiment for both endpoints.

EXAMPLE 7

Quantitative Expression Profiling

Expression profiling is based on a quantitative polymerase chain reaction (PCR) analysis, also called kinetic analysis, first described in Higuchi et al., 1992 and Higuchi et al., 1993. The principle is that at any given cycle within the exponential phase of PCR, the amount of product is proportional to the initial number of template copies. Using this technique, the expression levels of particular genes, which are transcribed from the chromosomes as messenger RNA (mRNA), are measured by first making a DNA copy (cDNA) of the mRNA, and then performing quantitative PCR on the cDNA, a method called quantitative reverse transcription-polymerase chain reaction (quantitative RT-PCR).

Quantitative RT-PCR analysis of RNA from different human tissues was performed to investigate the tissue distribution of LBRI-221 (SEQ ID NOS:2, 10, and 11), Ceramide kinase mRNA. In most cases, 25 µg of total RNA from various tissues (including Human Total RNA Panel I–V, Clontech Laboratories, Palo Alto, Calif., USA) was used as a template to synthesize first-strand cDNA using the SUPERSCRIPT™ First-Strand Synthesis System for RT-PCR (Life Technologies, Rockville, Md., USA).

First-strand cDNA synthesis was carried out according to the manufacturer's protocol using oligo (dT) to hybridize to the 3' poly A tails of mRNA and prime the synthesis reaction. Approximately 10 ng of the first-strand cDNA was then used as template in a polymerase chain reaction. In other cases, 10 ng of commercially available cDNAs (Human Immune System MTC Panel and Human Blood Fractions MTC Panel; Clontech Laboratories, Palo Alto, Calif., USA) were used as template in a polymerase chain reaction. The polymerase chain reaction was performed in a LightCycler (Roche Molecular Biochemicals, Indianapolis, Ind., USA), in the presence of the DNA-binding fluorescent dye SYBR Green I which binds to the minor groove of the DNA double helix, produced only when double-stranded DNA is successfully synthesized in the reaction (Morrison et al., 1998). Upon binding to double-stranded DNA, SYBR Green I emits light that can be quantitatively measured by the LightCycler machine.

The polymerase chain reaction was carried out using the oligonucleotide primers shown in SEQ ID NOS:12 and 13, and measurements of the intensity of emitted light were taken following each cycle of the reaction when the reaction had reached a temperature of 85° C. Intensities of emitted light were converted into copy numbers of the gene transcript per nanogram of template cDNA by comparison with simultaneously reacted standards of known concentration. to correct for differences in mRNA transcription levels per cell in the various tissue types, a normalization procedure was performed using similarly calculated expression levels in the various tissues of five different housekeeping genes: glyceraldehyde-3-phosphatase (G3PDH), hypoxanthine guanine phophoribosyl transferase (HPRT), beta-actin, porphobilinogen deaminase (PBGD), and beta-2-microglobulin. The level of housekeeping gene expression is considered to be relatively constant for all tissues (Adams et al., 1993, Adams et al., 1995, Liew et al., 1994) and therefore can be used as a gauge to approximate relative numbers of cells per mug of total RNA used in the cDNA synthesis step. Except for the use of a slightly different set of housekeeping genes and the use of the LightCycler system to measure expression levels, the normalization procedure was similar to that described in the RNA Master Blot User Manual, Appendix C (1997, Clontech Laboratories, Palo Alto, Calif., USA).

In brief, expression levels of the five housekeeping genes in all tissue samples were measured in three independent reactions per gene using the LightCycler and a constant amount (25 µg) of starting RNA. The calculated copy numbers for each gene, derived;-from comparison with simultaneously reacted standards of known concentrations; were recorded and the mean number of copies of each gene in all tissue samples was determined. Then for each tissue sample, the expression of each housekeeping gene relative to the mean was calculated, and the average of these values over the five housekeeping genes was found. A normalization factor for each tissue was then calculated by dividing the final value for one of the tissues arbitrarily selected as a standard by the corresponding value for each of the tissues. To normalize an experimentally obtained value for the expression of a particular gene in a tissue sample, the obtained value was multiplied by the normalization factor for the tissue tested. This normalization method was used for all tissues except those derived from the Human Blood Fractions MTC Panel, which showed dramatic variation in some housekeeping genes depending on whether the tissue had been activated or not. In these tissues, normalization was carried out with a single housekeeping gene, beta-2-microglobulin.

Results are SHOWN in FIGS. 3 and 4, showing the experimentally obtained copy numbers of mRNA per 10 ng of first-strand cDNA on the left and the normalized values on the right. RNAs used for the cDNA synthesis, along with their supplier and catalog numbers are shown in Tables 1 and 2.

TABLE 1

| Tissue | Supplier | Panel name and catalog number |
| --- | --- | --- |
| 1. brain | Clontech | Human Total RNA Panel I, K4000-1 |
| 2. heart | Clontech | Human Total RNA Panel I, K4000-1 |
| 3. kidney | Clontech | Human Total RNA Panel I, K4000-1 |
| 4. liver | Clontech | Human Total RNA Panel I, K4000-1 |
| 5. lung | Clontech | Human Total RNA Panel I, K4000-1 |
| 6. trachea | Clontech | Human Total RNA Panel I, K4000-1 |
| 7. bone marrow | Clontech | Human Total RNA Panel II, K4001-1 |
| 8. colon | Clontech | Human Total RNA Panel II, K4001-1 |
| 9. small intestine | Clontech | Human Total RNA Panel II, K4001-1 |
| 10. spleen | Clontech | Human Total RNA Panel II, K4001-1 |
| 11. stomach | Clontech | Human Total RNA Panel II, K4001-1 |
| 12. thymus | Clontech | Human Total RNA Panel II, K4001-1 |
| 13. mammary gland | Clontech | Human Total RNA Panel III, K4002-1 |
| 14. skeletal muscle | Clontech | Human Total RNA Panel III, K4002-1 |
| 15. prostate | Clontech | Human Total RNA Panel III, K4002-1 |
| 16. testis | Clontech | Human Total RNA Panel III, K4002-1 |
| 17. uterus | Clontech | Human Total RNA Panel III, K4002-1 |
| 18. cerebellum | Clontech | Human Total RNA Panel IV, K4003-1 |
| 19. fetal brain | Clontech | Human Total RNA Panel IV, K4003-1 |
| 20. fetal liver | Clontech | Human Total RNA Panel IV, K4003-1 |
| 21. spinal cord | Clontech | Human Total RNA Panel IV, K4003-1 |
| 22. placenta | Clontech | Human Total RNA Panel IV, K4003-1 |
| 23. adrenal gland | Clontech | Human Total RNA Panel V, K4004-1 |
| 24. pancreas | Clontech | Human Total RNA Panel V, K4004-1 |
| 25. salivary gland | Clontech | Human Total RNA Panel V, K4004-1 |
| 26. thyroid | Clontech | Human Total RNA Panel V, K4004-1 |

TABLE 2

| Tissue | Supplier | Panel name and catalog number |
| --- | --- | --- |
| 1. lymph node | Clontech | Human Immune System MTC Panel, K1426-1 |
| 2. peripheral blood leukocytes | Clontech | Human Immune System MTC Panel, K1426-1 |
| 3. tonsil | Clontech | Human Immune System MTC Panel, K1426-1 |
| 4. peripheral blood mononuclear cells | Clontech | Human Blood Fractions MTC Panel, K1428-1 |
| 5. peripheral blood mononuclear cells-activated | Clontech | Human Blood Fractions MTC Panel, K1428-1 |
| 6. T-cell (CD8+) | Clontech | Human Blood Fractions MTC Panel, K1428-1 |
| 7. T-cell (CD8+)-activated | Clontech | Human Blood Fractions MTC Panel, K1428-1 |
| 8. T-cell (CD4+) | Clontech | Human Blood Fractions MTC Panel, K1428-1 |
| 9. T-cell (CD4+)-activated | Clontech | Human Blood Fractions MTC Panel, K1428-1 |
| 10. B-cell (CD19+) | Clontech | Human Blood Fractions MTC Panel, K1428-1 |
| 11. B-cell (CD19+)-activated | Clontech | Human Blood Fractions MTC Panel, K1428-1 |
| 12. Monocytes (CD14+) | Clontech | Human Blood Fractions MTC Panel, K1428-1 |
| 13. Th1 clone | In-house | |
| 14. Th2 clone | In-house | |
| 15. neutrophil | In-house | |
| 16. neutrophil | In-house | |
| 17. Normal Bronchial/Tracheal Epithelial Cells | In-house | |
| 18. Normal Bronchial/Tracheal smooth muscle cell | In-house | |
| 19. Normal lung fibroblast | In-house | |
| 20. Microvascular Endothelial cell | In-house | |
| 21. U937 | In-house | |
| 22. RAMOS | In-house | |
| 23. Jurkat | In-house | |
| 24. HelaS3 | In-house | |
| 25. IMR-90 | In-house | |
| 26. HEK293 | In-house | |

EXAMPLE 8

In Vivo Testing of Compounds/Target Validation

Pain

Acute pain is measured on a hot plate mainly in rats. Two variants of hot plate testing are used: In the classical variant animals are put on a hot surface (52 to 56° C.) and the latency time is measured until the animals show nocifensive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t., i.c.v., s.c., intradermal, transdermal) prior to pain testing.

Persistent pain is measured with the formalin or capsaicin test, mainly in rats. A solution of 1 to 5% formalin or 10 to 100 µg capsaicin is injected into one hind paw of the experimental animal. After formalin or capsaicin application the animals show nocifensive reactions like flinching, licking and biting of the affected paw. The number of nocifensive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

Neuropathic pain. Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve. The second variant is the tight ligation of about the half of the diameter of the common sciatic nerve. In the next variant, a group of models is used in which tight ligations or transections are made of either the L5 and L6 spinal nerves, or the L % spinal nerve only. The fourth variant involves an axotomy of two of the three terminal branches of the sciatic nerve (tibial and common peroneal nerves) leaving, the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynioa, as well as a thermal hyperalgesia. Mechanical allodynia is measured by means of a pressure transducer (electronic von Frey Anesthesiometer, IITC Inc.-Life Science Instruments, Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10 ° C. where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadian rhythms in activity (Surjo and Arndt, Universität zu Köln, Cologne, Germany), and by scoring differences in gait (foot print patterns; FOOTPRINTS program, Klapdor et al., 1997. A low cost method to analyze footprint patterns. J. Neurosci. Methods 75, 49–54).

Compounds are tested against sham operated and vehicle treated control groups. Substance application is performed at different time points via different application routes (i.v., i.p., p.o., i.t., i.c.v., s.c., intradermal, transdermal) prior to pain testing.

Inflammatory pain. Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

Diabetic neuropathic pain. Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

Parkinson's Disease

6-Hydroxydopamine (6-OH-DA) Lesion. Degeneration of the dopaminergic nigrostriatal and striatopallidal pathways is the central pathological event in Parkinson's disease. This disorder has been mimicked experimentally in rats using single/sequential unilateral stereotaxic injections of 6-OH-DA into the medium forebrain bundle (MFB).

Male Wistar rats (Harlan Winkelmann, Germany), weighing 200±250 g at the beginning of the experiment, are used. The rats are maintained in a temperature- and humidity-controlled environment under a 12 h light/dark cycle with free access to food and water when not in experimental sessions. The following in vivo protocols are approved by the governmental authorities. All efforts are made to minimize animal suffering, to reduce the number of animals used, and to utilize alternatives to in vivo techniques.

Animals are administered pargyline on the day of surgery (Sigma, St. Louis, Mo., USA; 50 mg/kg i.p.) in order to inhibit metabolism of 6-OHDA by monoamine oxidase and desmethylimipramine HCl (Sigma; 25 mg/kg i.p.) in order to prevent uptake of 6-OHDA by noradrenergic terminals. Thirty minutes later the rats are anesthetized with sodium pentobarbital (50 mg/kg) and placed in a stereotaxic frame. In order to lesion the DA nigrostriatal pathway 4 µl of 0.01% ascorbic acid-saline containing 8 µg of 6-OHDA HBr (Sigma) are injected into the left medial fore-brain bundle at a rate of 1 µl/min (2.4 mm anterior, 1.49 mm lateral, −2.7 mm ventral to Bregma and the skull surface). The needle is left in place an additional 5 min to allow diffusion to occur.

Stepping Test

Forelimb akinesia is assessed three weeks following lesion placement using a modified stepping test protocol. In brief, the animals are held by the experimenter with one hand fixing the hindlimbs and slightly raising the hind part above the surface. One paw is touching the table, and is then moved slowly sideways (5 s for 1 m), first in the forehand and then in the backhand direction. The number of adjusting steps is counted for both paws in the backhand and forehand direction of movement. The sequence of testing is right paw forehand and backhand adjusting stepping, followed by left paw forehand and backhand directions. The test is repeated three times on three consecutive days, after an initial training period of three days prior to the first testing. Forehand adjusted stepping reveals no consistent differences between lesioned and healthy control animals. Analysis is therefore restricted to backhand adjusted stepping.

Balance Test

Balance adjustments following postural challenge are also measured during the stepping test sessions. The rats are held in the same position as described in the stepping test and, instead of being moved sideways, tilted by the experimenter towards the side of the paw touching the table. This maneuver results in loss of balance and the ability of the rats to regain balance by forelimb movements is scored on a scale ranging from 0 to 3. Score 0 is given for a normal forelimb placement. When the forelimb movement is delayed but recovery of postural balance detected, score 1 is given. Score 2 represents a clear, yet insufficient, forelimb reaction, as evidenced by muscle contraction, but lack of success in recovering balance, and score 3 is given for no reaction of movement. The test is repeated three times a day on each side for three consecutive days after an initial training period of three days prior to the first testing.

Staircase Test (Paw Reaching)

A modified version of the staircase test is used for evaluation of paw reaching behavior three weeks following primary and secondary lesion placement. Plexiglass test boxes with a central platform and a removable staircase on each side are used. The apparatus is designed such that only the paw on the same side at each staircase can be used, thus providing a measure of independent forelimb use. For each test the animals are left in the test boxes for 15 min. The double staircase is filled with 7×3 chow pellets (Precision food pellets, formula: P, purified rodent diet, size 45 mg; Sandown Scientific) on each side. After each test the number of pellets eaten (successfully retrieved pellets) and the number of pellets taken (touched but dropped) for each paw and the success rate (pellets eaten/pellets taken) are counted separately. After three days of food deprivation (12 g per animal per day) the animals are tested for 11 days. Full analysis is conducted only for the last five days.

MPTP treatment. The neurotoxin 1-methyl-4-phenyl-1,2,3,6-tetrahydro-pyridine (MPTP) causes degeneration of mesencephalic dopaminergic (DAergic) neurons in rodents, non-human primates, and humans and, in so doing, reproduces many of the symptoms of Parkinson's disease. MPTP leads to a marked decrease in the levels of dopamine and its metabolites, and in the number of dopaminergic terminals in the. striatum as well as severe loss of the tyrosine hydroxylase (TH)-immunoreactive cell bodies in the substantia nigra, pars compacta.

In order to obtain severe and long-lasting lesions, and to reduce mortality, animals receive single injections of MPTP, and are then tested for severity of lesion 7–10 days later. Successive MPTP injections are administered on days 1, 2 and 3. Animals receive application of 4 mg/kg MPTP hydrochloride (Sigma) in saline once daily. All injections are intraperitoneal (i.p.) and the MPTP stock solution is frozen between injections. Animals are decapitated on day 11.

Immunohistology

At the completion of behavioral experiments, all animals are anaesthetized with 3 ml thiopental (1 g/40 ml i.p., Tyrol Pharma). The mice are perfused transcardially with 0.01 M PBS (pH 7.4) for 2 min, followed by 4% paraformaldehyde (Merck) in PBS for 15 min. The brains are removed and placed in 4% paraformaldehyde for 24 h at 4° C. For dehydration they are then transferred to a 20% sucrose (Merck) solution in 0.1 M PBS at 4° C. until they sink. The brains are frozen in methylbutan at −20° C. for 2 min and stored. at −70° C. Using a sledge microtome (mod. 3800-Frigocut, Leica), 25 µm sections are taken from the genu of the corpus callosum (AP 1.7 mm) to the hippocampus (AP 21.8 mm) and from AP 24.16 to AP 26.72. Forty-six sections are cut and stored in assorters in 0.25 M Tris buffer (pH 7.4) for immunohistochemistry.

A series of sections is processed for free-floating tyrosine hydroxylase (TH) immunohistochemistry. Following three rinses in 0.1 M PBS, endogenous peroxidase activity is quenched for 10 min in 0.3% $H_2O_2$ ±PBS. After rinsing in PBS, sections are preincubated in 10% normal bovine serum (Sigma) for 5 min as blocking agent and transferred to either primary anti-rat TH rabbit antiserum (dilution 1:2000).

Following overnight incubation at room temperature, sections for TH immunoreactivity are rinsed in PBS (2×10 min) and incubated in biotinylated anti-rabbit immunoglobulin G raised in goat (dilution 1:200) (Vector) for 90 min, rinsed repeatedly and transferred to Vectastain ABC (Vector) solution for 1 h. 3,3'-Diaminobenzidine tetrahydrochloride (DAB; Sigma) in 0.1 M PBS, supplemented with 0.005% $H_2O_2$, serves as chromogen in the subsequent visualization reaction. Sections are mounted on to gelatin-coated slides, left to dry overnight, counter-stained with hematoxylin dehydrated in ascending alcohol concentrations and cleared in butylacetate. Coverslips are mounted on entellan.

Rotarod Test

We use a modification of the procedure described by Rozas and Labandeira-Garcia (1997), with a CR-1 Rotamex system (Columbus Instruments, Columbus, Ohio) comprising an IBM-compatible personal computer, a CIO-24 data acquisition card, a control unit, and a four-lane rotarod unit. The rotarod unit consists of a rotating spindle (diameter 7.3 cm) and individual compartments for each mouse. The system software allows preprogramming of session protocols with varying rotational speeds (0–80 rpm). Infrared beams are used to detect when a mouse has fallen onto the base grid beneath the rotarod. The system logs the fall as the end of the experiment for that mouse, and the total time on the rotarod, as well as the time of the fall and all the set-up parameters, are recorded. The system also allows a weak current to be passed through the base grid, to aid training.

Dementia

Object recognition task. The object recognition task has been designed to assess the effects of experimental manipulations on the cognitive performance of rodents. A rat is placed in an open field, in which two identical objects are present. The rats inspects both objects during the first trial of the object recognition task. In a second trial, after a retention interval of for example 24 hours, one of the two objects used in the first trial, the 'familiar' object, and a novel object are placed in the open field. The inspection time at each of the objects is registered. The basic measures in the OR task is the time spent by a rat exploring the two object the second trial. Good retention is reflected by higher exploration times towards the novel than the 'familiar' object.

Passive avoidance task. The passive avoidance task assesses memory performance in rats and mice. The inhibitory avoidance apparatus consists of a two-compartment box with a light compartment and a dark compartment. The two compartments are separated by a guillotine door that can be operated by the experimenter. A threshold of 2 cm separates the two compartments when the guillotine door is raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. In the habituation sessions and the retention session the rat is allowed to explore the apparatus for 300 sec. The rat is placed in the light compartment, facing the wall opposite to the guillotine door. After an accommodation period of 15 sec. the guillotine door is opened so that all parts of the apparatus can be visited freely. Rats normally avoid brightly lit areas and will enter the dark compartment within a few seconds.

In the shock session the guillotine door between the compartments is lowered as soon as the rat has entered the dark compartment with its four paws, and a scrambled 1 mA footshock is administered for 2 sec. The rat is removed from the apparatus and put back into its home cage. The procedure during the retention session is identical to that of the habituation sessions.

The step-through latency, that is the first latency of entering the dark compartment (in sec.) during the retention session is an index of the memory performance of the animal; the longer the latency to enter the dark compartment, the better the retention is. A testing compound in given half an hour before the shock session, together with 1 $mg*kg^{-1}$ scopolamine. Scopolamine impairs the memory performance during the retention session 24 hours later. If the test compound increases the enter latency compared with the scopolamine-treated controls, is likely to possess cognition enhancing potential.

Morris water escape task. The Morris water escape task measures spatial orientation learning in rodents. It is a test system that has extensively been used to investigate the effects of putative therapeutic on the cognitive functions of rats and mice. The performance of an animal is assessed in a circular water tank with an escape platform that is submerged about 1 cm below the surface of the water. The escape platform is not visible for an animal swimming in the water tank. Abundant extra-maze cues are provided by the furniture in the room, including desks, computer equipment, a second water tank, the presence of the experimenter, and by a radio on a shelf that is playing softly.

The animals receive four trials during five daily acquisition sessions. A trial is started by placing an animal into the pool, facing the wall of the tank. Each of four starting positions in the quadrants north, east, south, and west is used once in a series of four trials; their order is randomized. The escape platform is always in the same position. A trial is terminated as soon as the animal had climbs onto the escape platform or when 90 seconds have elapsed, whichever event occurs first. The animal is allowed to stay on the platform for 30 seconds. Then it is taken from the platform and the next trial is started. If an animal did not find the platform within 90 seconds it is put on the platform by the experimenter and is allowed to stay there for 30 seconds. After the fourth trial of the fifth daily session, an additional trial is given as a probe trial: the platform is removed, and the time the animal spends in the four quadrants is measured for 30 or 60 seconds. In the probe trial, all animals start from the same start position, opposite to the quadrant where the escape platform had been positioned during acquisition.

Four different measures are taken to evaluate the performance of an animal during acquisition training: escape latency, traveled distance, distance to platform, and swimming speed. The following measures are evaluated for the probe trial: time (s) in quadrants and traveled distance (cm) in the four quadrants. The probe trial provides additional information about how well an animal learned the position of the escape platform. If an animal spends more time and swims a longer distance in the quadrant where the platform had been positioned during the acquisition sessions than in any other quadrant, one concludes that the platform position has been learned well.

In order to assess the effects of putative cognition enhancing compounds, rats or mice with specific brain lesions which impair cognitive functions, or animals treated with compounds such as scopolamine or MK-801, which interfere with normal learning, or aged animals which suffer from cognitive deficits, are used.

T-maze spontaneous alternation task. The T-maze spontaneous alternation task (TeMCAT) assesses the spatial memory performance in mice. The start arm and the two goal arms of the T-maze are provided with guillotine doors which can be operated manually by the experimenter. A mouse is put into the start arm at the beginning of training. The guillotine door is closed. In the first trial, the 'forced trial', either the left or right goal arm is blocked by lowering the guillotine door. After the mouse has been released from the start arm, it will negotiate the maze, eventually enter the open goal arm, and return to the start position, where it will be confined for 5 seconds, by lowering the guillotine door. Then, the animal can choose freely between the left and right goal arm (all guillotine-doors opened) during 14 'free choice' trials. As soon a the mouse has entered one goal arm, the other one is closed. The mouse eventually returns to the start arm and is free to visit whichever go alarm it wants after having been confined to the start arm for 5 seconds. After completion of 14 free choice trials in one session, the animal is removed from the maze. During training, the animal is never handled.

The percent alternations out of 14 trials is calculated. This percentage and the total time needed to complete the first forced trial and the subsequent 14 free choice trials (in s) is analyzed. Cognitive deficits are usually induced by an injection of scopolamine, 30 min before the start of the training session. Scopolamine reduced the per-cent alternations to chance level, or below. A cognition enhancer, which is always administered before the training session, will at least partially, antagonize the scopolamine-induced reduction in the spontaneous alternation rate.

EXAMPLE 9

In Vivo Validation of Novel Compounds

Tests for activity of T cells are used to evaluate agents that modulate the expression or activity of costimulatory molecules-cytokines, cytokine receptors, signaling molecules, or other molecules involved in T cell activation.

Mouse Anti-CD3-Induced Cytokine Production Model

BALB/c mice are injected with a single intravenous injection of 10 μg of 145–2C11 (purified hamster anti-mouse CD3 monoclonal antibodies, PHARMINGEN). Compound is administered intraperitoneally 60 min prior to the anti-CD3 mAb injection. Blood is collected 90 min after the antibody injection. Serum is obtained by centrifugation at 3000 rpm for 10 min. Serum levels of cytokines, such as IL-2 and IL-4, or other secreted molecules are determined by an ELISA. Proteins which regulate the CD3 downstream signaling can be evaluated in this model.

Tests for activity of B cells are used to evaluate agents that modulate the expression or activity of the B cell receptor, signaling molecules, or other molecules involved in B cell activation/immunoglobulin class switching.

Mouse Anti-IgD Induced IgE Production Model

BALB/c mice are injected intravenously with 0.8 mg of purified goat anti-mouse IgD antibody or PBS (defined as day 0). Compound is administered intraperitoneally from day 0 to day 6. On day 7 blood is collected and serum is obtained by centrifugation at 3000 rpm for 10 min. Serum levels of total IgE are determined by YAMASA's ELISA kit and other Ig subtypes are measured by an Ig ELISA KIT (Rougier Bio-tech's, Montreal, Canada). Proteins that regulate IgD downstream signaling and Ig class switching can be evaluated.

Tests for activity of monocytes/macrophages are used to evaluate agents that modulate the expression or activity of signaling molecules, transcription factors.

Mouse LPS-Induced TNF-α Production Model

A compound is administered to BALB/c mice by intraperitoneal injection and one hour later the mice given LPS (200 µg/mouse) by intraperitoneal injection. Blood is collected 90 minutes after the LPS injection and plasma is obtained. TNF-α concentration in the sample is determined using an ELISA kit. Proteins that regulate downstream effects of LPS stimulation, such as NF-κB activation, can be evaluated.

Tests for activity of eosinophils are used to evaluate agents that modulate the expression or activity of the eotaxin receptor, signaling molecules, cytoskeletal molecules, or adhesion molecules.

Mouse Eotaxin-Induced Eosinophilia Model

BALB/c mice are injected intradermally with a 2.5 ml of air on days -6 and -3 to prepare an airpouch. On day 0, compound is administered intraperitoneally, and 30 minutes later, IL-5 (300 ng/mouse) is injected intravenously. After an additional 30 minutes, eotaxin is injected (3 µg/mouse, i.d.). Four hours after the eotaxin injection, leukocytes in the airpouch exudate are collected and the number of total cells is counted. Differential cell counts in the exudate are performed by staining with May-Grunwald Gimsa solution. Proteins that regulate signaling by the eotaxin receptor or regulate eosinophil trafficking can be evaluated.

Passive Cutaneous Anaphylaxis (PCA) Test in Rats

Six week-old male Wistar rats are sensitized intradermally (i.d.) on their shaved backs with 50 µl of 0.1 µg/ml mouse anti-DNP IgE monoclonal antibody (SPE-7) under a light anesthesia. After 24 hours, the rats are challenged intravenously with 1 ml of saline containing 0.6 mg DNP-BSA (30) (LSL CO., LTD) and 0.005 g of Evans blue. Compounds are injected intraperitoneally (i.p.) 0.5 hr prior to antigen injection. Rats without the sensitization, challenge, and compound treatment are used as a control and rats with sensitization, challenge and vehicle treatment are used to determine the value without inhibition. Thirty minutes after the challenge, the rats are sacrificed, and the skin of the back is removed. Evans blue dye in the skin is extracted in formamide overnight at 63° C. Absorbance at 620 nm is then measured to obtain the optical density of the leaked dye.

Percent inhibition of PCA with a compound is calculated as follows:

% inhibition={(mean vehicle value–sample value)/ (mean vehicle value–mean control value)}×100.

Proteins that regulate mast cell degranulation, vascular permeability, or receptor antagonists against histamine receptors, serotonin receptors, or cysteinyl leukotriene receptors can be evaluated.

Anaphylactic Bronchoconstriction in Rats

Six week-old male Wistar rats are sensitized intravenously (i.v.) with 10 µg mouse anti-DNP IgE, SPE-7, and 1 days later, the rats are challenged intravenously with 0.3 ml of saline containing 1.5 mg DNP-BSA (30) under anesthesia with urethane (1000 mg/kg, i.p.) and gallamine (50 mg/kg, i.v.). The trachea is cannulated for artificial respiration (2 ml/stroke, 70 strokes/min). Pulmonary inflation pressure (PIP) is recorded through a side-arm of the cannula connected to a pressure transducer. Changes in PIP reflect a change of both resistance and compliance of the lungs. To evaluate a compound, the compound is given i.v. 5 min before challenge.

Proteins that regulate mast cell degranulation, vascular permeability or receptor antagonists against histamine receptors, serotonin receptors, or cysteinyl leukotriene receptors can be evaluated. Proteins that regulate the contraction of smooth muscle can be also evaluated.

T Cell Adhesion to Smooth Muscle Cells or Endothelial Cells

A purified population of T cells is prepared by ficoll density centrifugation followed by separation on a nylon wool column, rosetting with sheep red blood cells, or using magnetic beads coated with antibodies. The T cells are activated with mitogen for 36 to 42 hours and labeled with $^3$H-thymidine during the last 16 hours of the activation. Airway smooth muscle cells or bronchial microvascular endothelial cells are obtained from lung transplant tissue, from bronchus resections from cancer patients, from cadavers, or as cell lines from commercial sources. If fresh tissue is used as the source of cells, the smooth muscle cells and endothelial cells can be isolated from tissue by dissection followed by digestion for 30–60 minutes in a solution containing 1.7 mM ethyleneglycol-bis-(beta-aminoethyl-ether)-N,N,N',N'-tetraacetic acid 640 U/ml collagenase, 10 mg/ml soybean trypsin inhibitor, and 10 U/ml elastase. The smooth muscle cells or endothelial cells are grown in 24-well tissue culture dishes until confluent and then treated with a test compound and inflammatory mediators, such as TNF-α, for 24 hours. To measure adhesion, $6\times10^5$ T cells are added per well and allowed to adhere for one hour at 37° C. Nonadherent cells are removed by washing six times gently with medium. Finally, the remaining adherent cells are lysed by adding 300 µl 1% Triton-X 100 in PBS to each well and quantitating the radioactivity in a scintillation counter. The percent binding is calculated as counts recovered from adherent cells/total input counts x 100%.

REFERENCES

1. Liu, et al., *J. Biol. Chem.*, 275: 19513–19520 (2000).
2. Baumruker, T. and E. E. Prieschl, *Int. Arch. Allergy Imunol.*, 122: 85–90 (2000).
3. Takeshita, et al., J, Biol. Chem., MOO2569200 (2000).
4. Ohta et al., *FEBS Letters* (1994), 355(3), 267–70.
5. R. Million et al., *Lancet* 1:812–816 (1984).
6. J. A Engelbrecht et al., *Arthritis and Rheumatism* 26(10): 1275–1278 (1983).
7. G. W. Cannon et al., *Arthritis and Rheumatism* 26(10): 1269–1274 (1983).
8. Simon and Mills, *N. Eng. J. Med.* 302(21):1179–1243 (1980).
9. W. Katz et al., *Ann. Int. Med.* 101:176–179 (1984).
10. W. F. Kean et al., *Arthritis and Rheumatism* 23(2): 158–164 (1980).
11. S. Nagata, *Advances in Immunology* 57:129–144 (1994).
12. R. N. Kolesnick et al., *Biochem. Cell Biol.* 72:471–474 (1994).
13. M. Verheij et al., *Nature* 380:75–79 (1996).
14. C. J. van Koppen et al, *J. Biol. Chem.* 217(4):2082–2087 (1996).
15. O. Cuvillier et al., *Nature* 381:800–803 (1996).
16. A. Abbas, *Cell* 84:655–657 (1996).
17. C. Jacob et al., *J. Immunol* 142(5):1500–1505 (1989).
18. K. Goodemote et al., *J. Biol. Chem.* 270:10272–10277 (1995).

19. G. H. Fisher et al., *Cell* 81:935–946 (1995).
20. F. Rieux-Laucat et al., *Science* 268:1347–1349 (1995).
21. M. Adachi et al., *Proc. Natl. Acad. Sci. (USA)* 90:1756–1760 (1993).
22. B. S. Andrews et al., *J. Exp. Med.* 148:1198–1215 (1978).
23. H. Takayama et al., *Adv. Immunol.* 60:289–321 (1995).
24. D. W. Nicholson et al., *Nature* 376:37–43 (1995).
25. M. Tewari et al., *Cell* 81:801–869 (1995).
26. A. M. Chinnaiyan et al., *Cell* 81:505–512 (1995).
27. S. M. Krane and R. T. Salzman, *Am J. Med.*: 75(4B): 1–91(1983).
28. D. E. Furst, *Arth. & Rheum.* 37(1):1–9 (1994).
29. B. O. Barger et al., *Arth. & Rheum.* 27(6):601–605 (June 1984).
30. H. B. Stein et al., *Ann. Int. Med.* 92:24–29 (1980).
31. C. J. Marshall, *Nature* 367:686 (1994).
32. G. L'Allemain, *Progress in Growth Factor Research* 5:291–334 (1994).
33. S. A. Susin et al., *J. Exp. Med.* 186(1):25–37 (1997).
34. Higuchi, R., Dollinger, G., Walsh, P. S. and Griffith, R. (1992) Simultaneous amplification and detection of specific DNA sequences. *BioTechnology* 10:413–417.
35. Higuchi, R., Fockler, C., Dollinger, G. and Watson, R. (1993) Kinetic PCR analysis: real-time monitoring of DNA amplification reactions. *BioTechnology* 11:1026–1030.
36. T. B. Morrison, J. J. Weis & C. T. Wittwer (1998) Quantification of low-copy transcripts by continuous SYBR Green I monitoring during amplification. *Biotechniques* 24:954–962.
37. Adams, M. D., Kerlavage, A. R., Fields, C. & Venter, C. (1993) 3,400 new expressed sequence tags identify diversity of transcripts in human brain. *Nature Genet.* 4:256–265.
38. Adams, M. D., et al. (1995) Initial assessment of human gene diversity and expression patterns based upon 83 million nucleotides of cDNA sequence. *Nature* 377 supp: 3–174.
39. Liew, C. C., Hwang, D. M., Fung, Y. W., Laurenson, C., Cukerman, E., Tsui, S. & Lee, C. Y. (1994) A catalog of genes in the cardiovascular system as identified by expressed sequence tags. *Proc. Natl. Acad. Sci. USA* 91:10145–10649.

The invention claimed is:

1. A purified polypeptide comprising an amino acid sequence selected from the group consisting of the amino acid sequences shown in SEQ ID NOS:10, and 11 and.

2. The purified polypeptide of claim 1 which comprises the amino acid sequence shown in SEQ ID NO:10.

3. The purified polypeptide of claim 1 which comprises the amino acid sequence shown in SEQ ID NO:11.

4. A fusion protein comprising a polypeptide consisting of an amino acid sequence selected from the group consisting of the amino acid sequence shown in SEQ ID NOS:10, and 11.

5. A kit for detecting a polypeptide comprising an amino acid sequence selected from the group consisting of an amino acid sequence selected from the group consisting of SEQ ID NOS:10, and 11, comprising:

an antibody which specifically binds to the polypeptide; and instructions for the method of detecting said polypeptide comprising the steps of: contacting a biological sample with said antibody to form a reagent-polypeptide complex; and detecting the antibody-polypeptide complex.

* * * * *

UNITED STATES PATENT AND TRADEMARK OFFICE
CERTIFICATE OF CORRECTION

| | | |
|---|---|---|
| PATENT NO. | : 7,037,700 B2 | Page 1 of 1 |
| APPLICATION NO. | : 10/631958 | |
| DATED | : May 2, 2006 | |
| INVENTOR(S) | : Sophia Kossida et al. | |

It is certified that error appears in the above-identified patent and that said Letters Patent is hereby corrected as shown below:

On the cover page, Filed section (22):
    Please replace "Dec. 19, 2003" with --Aug. 1, 2003--

In Column 71, Claim 1, Line 4:
    Please remove "and"

Signed and Sealed this

Nineteenth Day of September, 2006

JON W. DUDAS
*Director of the United States Patent and Trademark Office*

SEQUENCE LISTING

<160> NUMBER OF SEQ ID NOS: 16

<210> SEQ ID NO 1
<211> LENGTH: 979
<212> TYPE: DNA
<213> ORGANISM: Homo sapiens

<400> SEQUENCE: 1

```
accaaagcat ttactggtat ttatcaaccc gtttggagga aaaggacaag gcaagcggat      60
atatgaaaga aaagtggcac cactgttcac cttagcctcc atcaccactg acatcatcgg     120
taacaaattc tatgttaact atgtagaagt aattactgaa catgctaatc aggccaagga     180
gactctgtat gagattaaca tagacaaata cgacggcatc gtctgtgtcg gcggagatgg     240
tatgttcagc gaggtgctgc acggtctgat tgggaggacg cagaggagcg ccggggtcga     300
ccagaaccac ccccgggctg tgctggtccc cagtagcctc cggattggaa tcattcccgc     360
agggtcaacg gactgcgtgt gttactccac cgtgggcacc agcgacgcag aaacctcggc     420
gctgcatatc gttgttgggg actcgctggc catggatgtg tcctcagtcc accacaacag     480
cacactcctt cgctactccg tgtccctgct gggctacggc ttctacgggg acatcatcaa     540
ggacagtgag aagaaacggt ggttgggtct tgccagatac gacttttcag gtttaaagac     600
cttcctctcc caccactgct atgaagggac agtgtccttc ctccctgcac aacacacggt     660
gggatctcca agggatagga agccctgccg ggcaggatgc tttgtttgca ggcaaagcaa     720
gcagcagctg gaggaggagc agaagaaagc actgtatggt ttggaagctg cggaggacgt     780
ggaggagtgg caagtcgtct gtgggaagtt tctggccatc aatgccacaa acatgtcctg     840
tgcttgtcgc cggagcccca ggggcctctc cccggctgcc cacttgggag acgggtcttc     900
tgacctcatc ctcatccgga aatgctccag gttcaattttt ctgagatttc tcatcaggca     960
caccaaccag caggaccag                                                 979
```

<210> SEQ ID NO 2
<211> LENGTH: 326

<212> TYPE: PRT
<213> ORGANISM: Homo sapiens

<400> SEQUENCE: 2

```
Pro Lys His Leu Leu Val Phe Ile Asn Pro Phe Gly Lys Gly Gln
 1               5                  10                  15

Gly Lys Arg Ile Tyr Glu Arg Lys Val Ala Pro Leu Phe Thr Leu Ala
            20                  25                  30

Ser Ile Thr Thr Asp Ile Ile Gly Asn Lys Phe Tyr Val Asn Tyr Val
        35                  40                  45

Glu Val Ile Thr Glu His Ala Asn Gln Ala Lys Glu Thr Leu Tyr Glu
    50                  55                  60

Ile Asn Ile Asp Lys Tyr Asp Gly Ile Val Cys Val Gly Asp Gly
65                  70                  75                  80

Met Phe Ser Glu Val Leu His Gly Leu Ile Gly Arg Thr Gln Arg Ser
                85                  90                  95

Ala Gly Val Asp Gln Asn His Pro Arg Ala Val Leu Val Pro Ser Ser
            100                 105                 110

Leu Arg Ile Gly Ile Ile Pro Ala Gly Ser Thr Asp Cys Val Cys Tyr
        115                 120                 125

Ser Thr Val Gly Thr Ser Asp Ala Glu Thr Ser Ala Leu His Ile Val
    130                 135                 140

Val Gly Asp Ser Leu Ala Met Asp Val Ser Ser Val His His Asn Ser
145                 150                 155                 160

Thr Leu Leu Arg Tyr Ser Val Ser Leu Leu Gly Tyr Gly Phe Tyr Gly
                165                 170                 175

Asp Ile Ile Lys Asp Ser Glu Lys Lys Arg Trp Leu Gly Leu Ala Arg
            180                 185                 190

Tyr Asp Phe Ser Gly Leu Lys Thr Phe Leu Ser His His Cys Tyr Glu
        195                 200                 205

Gly Thr Val Ser Phe Leu Pro Ala Gln His Thr Val Gly Ser Pro Arg
    210                 215                 220

Asp Arg Lys Pro Cys Arg Ala Gly Cys Phe Val Cys Arg Gln Ser Lys
225                 230                 235                 240

Gln Gln Leu Glu Glu Glu Gln Lys Lys Ala Leu Tyr Gly Leu Glu Ala
                245                 250                 255

Ala Glu Asp Val Glu Glu Trp Gln Val Val Cys Gly Lys Phe Leu Ala
            260                 265                 270

Ile Asn Ala Thr Asn Met Ser Cys Ala Cys Arg Arg Ser Pro Arg Gly
        275                 280                 285

Leu Ser Pro Ala Ala His Leu Gly Asp Gly Ser Ser Asp Leu Ile Leu
    290                 295                 300

Ile Arg Lys Cys Ser Arg Phe Asn Phe Leu Arg Phe Leu Ile Arg His
305                 310                 315                 320

Thr Asn Gln Gln Asp Gln
                325
```

<210> SEQ ID NO 3
<211> LENGTH: 638
<212> TYPE: PRT
<213> ORGANISM: Homo sapiens

<400> SEQUENCE: 3

```
Met Ala Pro Pro Pro Pro Leu Ala Ala Ser Thr Pro Leu Leu His
 1               5                  10                  15
```

```
Gly Glu Phe Gly Ser Tyr Pro Ala Arg Gly Pro Arg Phe Ala Leu Thr
         20              25                  30

Leu Thr Ser Gln Ala Leu His Ile Gln Arg Leu Arg Pro Phe Thr Lys
         35              40                  45

Pro Glu Ala Arg Pro Arg Gly Gly Leu Val Pro Leu Ala Glu Val Ser
 50              55                  60

Gly Cys Cys Thr Leu Arg Ser Arg Ser Pro Ser Asp Ser Ala Ala Tyr
 65              70                  75                  80

Phe Cys Ile Tyr Thr Tyr Pro Arg Gly Arg Gly Ala Arg Arg Arg
             85                  90                  95

Ala Thr Arg Thr Phe Arg Ala Asp Gly Ala Phe Ala Thr Tyr Glu
             100                 105                 110

Glu Asn Arg Ala Glu Ala Gln Arg Trp Ala Thr Ala Leu Thr Cys Leu
         115                 120                 125

Leu Arg Gly Leu Pro Leu Pro Gly Asp Gly Glu Ile Thr Pro Asp Leu
         130                 135                 140

Leu Pro Arg Pro Pro Arg Leu Leu Leu Val Asn Pro Phe Gly Gly
145                 150                 155                 160

Arg Gly Leu Ala Trp Gln Trp Phe Thr Cys Lys Asn His Val Leu Pro
             165                 170                 175

Met Ile Ser Glu Ala Gly Leu Ser Phe Asn Leu Ile Gln Thr Glu Arg
         180                 185                 190

Gln Asn His Ala Arg Glu Leu Val Gln Gly Leu Ser Leu Ser Glu Trp
         195                 200                 205

Asp Gly Ile Val Thr Val Ser Gly Asp Gly Leu Leu His Glu Val Leu
         210                 215                 220

Asn Gly Leu Leu Phe Thr Asp Arg Pro Asp Trp Glu Glu Ala Val Lys
225                 230                 235                 240

Met Pro Val Gly Ile Leu Pro Cys Gly Ser Gly Asn Ala Leu Ala Gly
             245                 250                 255

Ala Val Asn Gln His Gly Gly Phe Glu Pro Ala Leu Gly Leu Asp Leu
         260                 265                 270

Leu Leu Asn Cys Ser Leu Leu Leu Cys Arg Gly Gly His Pro Leu
         275                 280                 285

Asp Phe Thr Leu Leu Ser Val Thr Leu Ala Ser Gly Ser Arg Cys Phe
         290                 295                 300

Ser Phe Leu Ser Val Ala Trp Gly Phe Val Ser Asp Val Asp Ile Gln
305                 310                 315                 320

Ser Glu Arg Phe Arg Ala Leu Gly Ser Ala Arg Phe Thr Leu Gly Thr
             325                 330                 335

Val Leu Gly Leu Ala Thr Leu His Thr Tyr Arg Gly Arg Leu Phe Thr
         340                 345                 350

Ser Tyr Leu Pro Ala Thr Val Glu Pro Ala Ser Pro Thr Pro Ala His
         355                 360                 365

Ser Leu Pro Arg Ala Lys Ser Glu Leu Thr Leu Thr Pro Asp Pro Ala
         370                 375                 380

Pro Pro Met Ala His Ser Pro Leu His Arg Ser Val Ser Asp Leu Pro
385                 390                 395                 400

Leu Pro Leu Pro Gln Pro Ala Leu Ala Ser Pro Phe Thr Gly Ser Pro
             405                 410                 415

Glu Pro Leu Pro Ile Leu Ser Leu Asn Gly Gly Pro Glu Leu Ala
             420                 425                 430

Gly Asp Trp Gly Gly Ala Gly Asp Ala Pro Leu Ser Pro Asp Pro Leu
```

```
                435                 440                 445
Leu Ser Ser Pro Pro Gly Ser Pro Lys Ala Ala Leu His Ser Pro Val
            450                 455                 460

Ser Glu Gly Ala Pro Val Ile Pro Phe Thr Pro Ser Ser Gly Leu Pro
465                 470                 475                 480

Leu Pro Thr Pro Asp Ala Arg Val Gly Ala Ser Thr Cys Gly Pro Pro
                485                 490                 495

Asp His Leu Leu Pro Pro Leu Gly Thr Pro Leu Pro Asp Trp Val
            500                 505                 510

Thr Leu Glu Gly Asp Phe Val Leu Met Leu Ala Ile Ser Pro Ser His
            515                 520                 525

Leu Gly Ala Asp Leu Phe Thr Val Ala Ala Pro His Ala Arg Phe Asp
            530                 535                 540

Asp Gly Leu Val His Leu Cys Trp Val Arg Ser Gly Ile Ser Arg Ala
545                 550                 555                 560

Ala Leu Leu Arg Leu Phe Leu Ala Met Glu Arg Gly Ser His Phe Ser
                565                 570                 575

Leu Gly Cys Pro Gln Leu Gly Tyr Ala Ala Arg Ala Phe Arg Leu
            580                 585                 590

Glu Pro Phe Thr Leu Thr Pro Arg Gly Val Leu Thr Val Asp Gly Glu
                595                 600                 605

Gln Val Glu Tyr Gly Pro Leu Gln Ala Gln Met His Pro Gly Ile Gly
            610                 615                 620

Thr Leu Leu Thr Gly Pro Pro Gly Cys Pro Gly Arg Glu Pro
625                 630                 635

<210> SEQ ID NO 4
<211> LENGTH: 474
<212> TYPE: DNA
<213> ORGANISM: Homo sapiens

<400> SEQUENCE: 4 cacgagggt atgttcagcg aggtgctgca cggtctgatt gggaggacgc agaggagcgc      60
cggggtcgac cagaaccacc cccgggctgt gctggtcccc agtagcctcc ggattggaat    120
cattcccgca gggtcaacgg actgcgtgtg ttactccacc gtgggcacca gcgacgcaga    180
aacctcggcg ctgcatatcg ttgttgggga ctcgctggcc atggatgtgt cctcagtcca    240
ccacaacagc acactccttc gctactccgt gtccctgctg ggctacggct tctacgggga    300
catcatcaag gacagtgaga agaaacggtg gttgggtctt gccagatacg acttttcagg    360
tttaaagacc ttcctctccc accactgcta tgaagggaca gtgtccttcc tccctgcaca    420
acacacggtg ggatctccaa gggataggaa gccctgccgg gcaagatgct ttgg          474

<210> SEQ ID NO 5
<211> LENGTH: 329
<212> TYPE: DNA
<213> ORGANISM: Homo sapiens
<220> FEATURE:
<221> NAME/KEY: misc_feature
<222> LOCATION: (1)...(329)
<223> OTHER INFORMATION: n = A,T,C or G

<400> SEQUENCE: 5
tcaccactga catcatcgtt actgaacatg ctantcaggc canggagact ctgtatgaga      60
ttaacataga caaatacgac ggcatcgtct gtgtcggcgg agatggtatg ttcagcgagg    120
tgctgcacgg tctgattggg aggacgcaga ggagcgccgg ggtcgaccag aaccacccc     180
```

| | |
|---|---|
| gggctgtgct ggtccccagt agcctccgga ttggaatcat tcccgcaggt caaacggact | 240 |
| gcgtgtntta ctccaccgtg ggcancagcg acgcagaaac ctcggcgctg catatcgttg | 300 |
| ttggggactc gctggccatg gatgtgtcc | 329 |

<210> SEQ ID NO 6
<211> LENGTH: 167
<212> TYPE: DNA
<213> ORGANISM: Homo sapiens

<400> SEQUENCE: 6

| | |
|---|---|
| gtttaaagac cttcctctcc caccactgct atgaagggac agtgtccttc ctccctgcac | 60 |
| aacacacggt gggatctcca agggatagga agccctgccg ggcaggatgc tttgtttgca | 120 |
| ggcaaagcaa gcagcagctg gaggaggagc agaagaaagc actgtat | 167 |

<210> SEQ ID NO 7
<211> LENGTH: 153
<212> TYPE: DNA
<213> ORGANISM: Homo sapiens

<400> SEQUENCE: 7

| | |
|---|---|
| gggactcgct ggccatggat gtgtcctcag tccaccacaa cagcacactc cttcgctact | 60 |
| ccgtgtccct gctgggctac ggcttctacg gggacatcat caaggacagt gagaagaaac | 120 |
| ggtggttggg tcttgccaga tacgactttt cag | 153 |

<210> SEQ ID NO 8
<211> LENGTH: 550
<212> TYPE: DNA
<213> ORGANISM: Homo sapiens

<400> SEQUENCE: 8

| | |
|---|---|
| cacgaggccg ctaacggtcc ggcgcccctc ggcgtccgcg cgcccccagc ctggcggacg | 60 |
| agcccggcgg cggagatggg ggcgacgggg gcggcggagc cgctgcaatc cgtgctgtgg | 120 |
| gtgaagcagc agcgctgcgc cgtgagcctg agcccgcgc gggctctgct gcgctggtgg | 180 |
| cggagcccgg ggcccggagc cggcgccccc ggcgcggatg cctgctctgt gcctgtatct | 240 |
| gagatcatcg ccgttgagga acagacgtt cacgggaaac atcaaggcag tggaaaatgg | 300 |
| cagaaaatgg aaaagcctta cgcttttaca gttcactgtg taaagagagc acgacggcac | 360 |
| cgctggaagt gggcgcaggt gactttctgg tgtccagagg agcagctgtg tcacttgtgg | 420 |
| ctgcagaccc tgcgggagat gctggagaag ctgacgtcca gaccaaagca tttactggta | 480 |
| tttatcaacc cgtttggagg aaaaggacaa ggcaagcgga tatatgaaag aaaagtggca | 540 |
| ccactgttca | 550 |

<210> SEQ ID NO 9
<211> LENGTH: 1614
<212> TYPE: DNA
<213> ORGANISM: Homo sapiens

<400> SEQUENCE: 9

| | |
|---|---|
| atggggggcga cggggggcggc ggagccgctg caatccgtgc tgtgggtgaa gcagcagcgc | 60 |
| tgcgccgtga gcctggagcc cgcgcgggct ctgctgcgct ggtggcggag cccggggccc | 120 |
| ggagccggcg cccccggcgc ggatgcctgc tctgtgcctg tatctgagat catcgccgtt | 180 |
| gaggaaacag acgttcacgg gaaacatcaa ggcagtggaa aatggcagaa aatggaaaag | 240 |

-continued

| | |
|---|---|
| ccttacgctt ttacagttca ctgtgtaaag agagcacgac ggcaccgctg aagtgggcg | 300 |
| caggtgactt tctggtgtcc agaggagcag ctgtgtcact tgtggctgca gaccctgcgg | 360 |
| gagatgctgg agaagctgac gtccagacca aagcatttac tggtatttat caacccgttt | 420 |
| ggaggaaaag gacaaggcaa gcggatatat gaaagaaaag tggcaccact gttcaccta | 480 |
| gcctccatca ccactgacat catcgttact gaacatgcta atcaggccaa ggagactctg | 540 |
| tatgagatta acatagacaa atacgacggc atcgtctgtg tcggcggaga tggtatgttc | 600 |
| agcgaggtgc tgcacggtct gattgggagg acgcagagga gcgccggggt cgaccagaac | 660 |
| cacccccggg ctgtgctggt ccccagtagc ctccggattg gaatcattcc cgcagggtca | 720 |
| acggactgcg tgtgttactc caccgtgggc accagcgacg cagaaacctc ggcgctgcat | 780 |
| atcgttgttg gggactcgct ggccatggat gtgtcctcag tccaccacaa cagcacactc | 840 |
| cttcgctact ccgtgtccct gctgggctac ggcttctacg ggacatcat caaggacagt | 900 |
| gagaagaaac ggtggttggg tcttgccaga tacgactttt caggttttaaa gaccttcctc | 960 |
| tcccaccact gctatgaagg gacagtgtcc ttcctccctg cacaacacac ggtgggatct | 1020 |
| ccaagggata ggaagccctg ccgggcagga tgctttgttt gcaggcaaag caagcagcag | 1080 |
| ctggaggagg agcagaagaa agcactgtat ggtttggaag ctgcggagga cgtggaggag | 1140 |
| tgcaagtcg tctgtgggaa gtttctggcc atcaatgcca caaacatgtc ctgtgcttgt | 1200 |
| cgccggagcc ccaggggcct ctccccggct gcccacttgg gagacgggtc ttctgacctc | 1260 |
| atcctcatcc ggaaatgctc caggttcaat tttctgagat ttctcatcag gcacaccaac | 1320 |
| cagcaggacc agtttgactt cactttttgtt gaagtttatc gcgtcaagaa attccagttt | 1380 |
| acgtcgaagc acatggagga tgaggacagc gacctcaagg agggggggaa gaagcgcttt | 1440 |
| gggcacattt gcagcagcca cccctcctgc tgctgcaccg tctccaacag ctcctggaac | 1500 |
| tgcgacgggg aggtcctgca cagccctgcc atcgaggtca gagtccactg ccagctggtt | 1560 |
| cgactctttg cacgaggaat tgaagagaat ccgaagccag actcacacag ctga | 1614 |

<210> SEQ ID NO 10
<211> LENGTH: 537
<212> TYPE: PRT
<213> ORGANISM: Homo sapiens

<400> SEQUENCE: 10

Met Gly Ala Thr Gly Ala Ala Glu Pro Leu Gln Ser Val Leu Trp Val
 1               5                  10                  15

Lys Gln Gln Arg Cys Ala Val Ser Leu Glu Pro Ala Arg Ala Leu Leu
             20                  25                  30

Arg Trp Trp Arg Ser Pro Gly Pro Gly Ala Gly Ala Pro Gly Ala Asp
         35                  40                  45

Ala Cys Ser Val Pro Val Ser Glu Ile Ile Ala Val Glu Glu Thr Asp
     50                  55                  60

Val His Gly Lys His Gln Gly Ser Gly Lys Trp Gln Lys Met Glu Lys
 65                  70                  75                  80

Pro Tyr Ala Phe Thr Val His Cys Val Lys Arg Ala Arg Arg His Arg
                 85                  90                  95

Trp Lys Trp Ala Gln Val Thr Phe Trp Cys Pro Glu Glu Gln Leu Cys
            100                 105                 110

His Leu Trp Leu Gln Thr Leu Arg Glu Met Leu Glu Lys Leu Thr Ser
        115                 120                 125

Arg Pro Lys His Leu Leu Val Phe Ile Asn Pro Phe Gly Gly Lys Gly

```
            130                 135                 140
Gln Gly Lys Arg Ile Tyr Glu Arg Lys Val Ala Pro Leu Phe Thr Leu
145                 150                 155                 160
Ala Ser Ile Thr Thr Asp Ile Ile Val Thr Glu His Ala Asn Gln Ala
                    165                 170                 175
Lys Glu Thr Leu Tyr Glu Ile Asn Ile Asp Lys Tyr Asp Gly Ile Val
                180                 185                 190
Cys Val Gly Gly Asp Gly Met Phe Ser Glu Val Leu His Gly Leu Ile
                195                 200                 205
Gly Arg Thr Gln Arg Ser Ala Gly Val Asp Gln Asn His Pro Arg Ala
            210                 215                 220
Val Leu Val Pro Ser Ser Leu Arg Ile Gly Ile Ile Pro Ala Gly Ser
225                 230                 235                 240
Thr Asp Cys Val Cys Tyr Ser Thr Val Gly Thr Ser Asp Ala Glu Thr
                    245                 250                 255
Ser Ala Leu His Ile Val Val Gly Asp Ser Leu Ala Met Asp Val Ser
                260                 265                 270
Ser Val His His Asn Ser Thr Leu Leu Arg Tyr Ser Val Ser Leu Leu
            275                 280                 285
Gly Tyr Gly Phe Tyr Gly Asp Ile Ile Lys Asp Ser Glu Lys Lys Arg
290                 295                 300
Trp Leu Gly Leu Ala Arg Tyr Asp Phe Ser Gly Leu Lys Thr Phe Leu
305                 310                 315                 320
Ser His His Cys Tyr Glu Gly Thr Val Ser Phe Leu Pro Ala Gln His
                    325                 330                 335
Thr Val Gly Ser Pro Arg Asp Arg Lys Pro Cys Arg Ala Gly Cys Phe
                340                 345                 350
Val Cys Arg Gln Ser Lys Gln Gln Leu Glu Glu Glu Gln Lys Lys Ala
            355                 360                 365
Leu Tyr Gly Leu Glu Ala Ala Glu Asp Val Glu Glu Trp Gln Val Val
            370                 375                 380
Cys Gly Lys Phe Leu Ala Ile Asn Ala Thr Asn Met Ser Cys Ala Cys
385                 390                 395                 400
Arg Arg Ser Pro Arg Gly Leu Ser Pro Ala Ala His Leu Gly Asp Gly
                405                 410                 415
Ser Ser Asp Leu Ile Leu Ile Arg Lys Cys Ser Arg Phe Asn Phe Leu
                420                 425                 430
Arg Phe Leu Ile Arg His Thr Asn Gln Gln Asp Gln Phe Asp Phe Thr
            435                 440                 445
Phe Val Glu Val Tyr Arg Val Lys Lys Phe Gln Phe Thr Ser Lys His
450                 455                 460
Met Glu Asp Glu Asp Ser Asp Leu Lys Glu Gly Gly Lys Lys Arg Phe
465                 470                 475                 480
Gly His Ile Cys Ser Ser His Pro Ser Cys Cys Thr Val Ser Asn
                    485                 490                 495
Ser Ser Trp Asn Cys Asp Gly Glu Val Leu His Ser Pro Ala Ile Glu
                500                 505                 510
Val Arg Val His Cys Gln Leu Val Arg Leu Phe Ala Arg Gly Ile Glu
            515                 520                 525
Glu Asn Pro Lys Pro Asp Ser His Ser
530                 535
```

<210> SEQ ID NO 11

```
<211> LENGTH: 562
<212> TYPE: PRT
<213> ORGANISM: Homo sapiens

<400> SEQUENCE: 11
```

| | | | | | | | | | | | | | | |
|---|---|---|---|---|---|---|---|---|---|---|---|---|---|---|
|His|Glu|Ala|Ala|Asn|Gly|Pro|Ala|Pro|Leu|Gly|Val|Arg|Ala|Pro|Pro|
|1| | | |5| | | | |10| | | | |15| |

Ala Trp Arg Thr Ser Pro Ala Ala Glu Met Gly Ala Thr Gly Ala Ala
                20                  25                  30

Glu Pro Leu Gln Ser Val Leu Trp Val Lys Gln Gln Arg Cys Ala Val
             35                  40                  45

Ser Leu Glu Pro Ala Arg Ala Leu Leu Arg Trp Trp Arg Ser Pro Gly
 50                  55                  60

Pro Gly Ala Gly Ala Pro Gly Ala Asp Ala Cys Ser Val Pro Val Ser
 65                  70                  75                  80

Glu Ile Ile Ala Val Glu Glu Thr Asp Val His Gly Lys His Gln Gly
                 85                  90                  95

Ser Gly Lys Trp Gln Lys Met Glu Lys Pro Tyr Ala Phe Thr Val His
                100                 105                 110

Cys Val Lys Arg Ala Arg Arg His Arg Trp Lys Trp Ala Gln Val Thr
                115                 120                 125

Phe Trp Cys Pro Glu Glu Gln Leu Cys His Leu Trp Leu Gln Thr Leu
130                 135                 140

Arg Glu Met Leu Glu Lys Leu Thr Ser Arg Pro Lys His Leu Leu Val
145                 150                 155                 160

Phe Ile Asn Pro Phe Gly Gly Lys Gly Gln Gly Lys Arg Ile Tyr Glu
                165                 170                 175

Arg Lys Val Ala Pro Leu Phe Thr Leu Ala Ser Ile Thr Thr Asp Ile
                180                 185                 190

Ile Val Thr Glu His Ala Asn Gln Ala Lys Glu Thr Leu Tyr Glu Ile
                195                 200                 205

Asn Ile Asp Lys Tyr Asp Gly Ile Val Cys Val Gly Gly Asp Gly Met
210                 215                 220

Phe Ser Glu Val Leu His Gly Leu Ile Gly Arg Thr Gln Arg Ser Ala
225                 230                 235                 240

Gly Val Asp Gln Asn His Pro Arg Ala Val Leu Val Pro Ser Ser Leu
                245                 250                 255

Arg Ile Gly Ile Ile Pro Ala Gly Ser Thr Asp Cys Val Cys Tyr Ser
                260                 265                 270

Thr Val Gly Thr Ser Asp Ala Glu Thr Ser Ala Leu His Ile Val Val
                275                 280                 285

Gly Asp Ser Leu Ala Met Asp Val Ser Ser Val His His Asn Ser Thr
                290                 295                 300

Leu Leu Arg Tyr Ser Val Ser Leu Leu Gly Tyr Gly Phe Tyr Gly Asp
305                 310                 315                 320

Ile Ile Lys Asp Ser Glu Lys Lys Arg Trp Leu Gly Leu Ala Arg Tyr
                325                 330                 335

Asp Phe Ser Gly Leu Lys Thr Phe Leu Ser His His Cys Tyr Glu Gly
                340                 345                 350

Thr Val Ser Phe Leu Pro Ala Gln His Thr Val Gly Ser Pro Arg Asp
                355                 360                 365

Arg Lys Pro Cys Arg Ala Gly Cys Phe Val Cys Arg Gln Ser Lys Gln
370                 375                 380

Gln Leu Glu Glu Glu Gln Lys Lys Ala Leu Tyr Gly Leu Glu Ala Ala

```
                385                 390                 395                 400
Glu Asp Val Glu Glu Trp Gln Val Val Cys Gly Lys Phe Leu Ala Ile
                    405                 410                 415
Asn Ala Thr Asn Met Ser Cys Ala Cys Arg Arg Ser Pro Arg Gly Leu
                420                 425                 430
Ser Pro Ala Ala His Leu Gly Asp Gly Ser Ser Asp Leu Ile Leu Ile
                435                 440                 445
Arg Lys Cys Ser Arg Phe Asn Phe Leu Arg Phe Leu Ile Arg His Thr
            450                 455                 460
Asn Gln Gln Asp Gln Phe Asp Phe Thr Phe Val Glu Val Tyr Arg Val
465                 470                 475                 480
Lys Lys Phe Gln Phe Thr Ser Lys His Met Glu Asp Glu Asp Ser Asp
                    485                 490                 495
Leu Lys Glu Gly Gly Lys Lys Arg Phe Gly His Ile Cys Ser Ser His
                500                 505                 510
Pro Ser Cys Cys Cys Thr Val Ser Asn Ser Ser Trp Asn Cys Asp Gly
            515                 520                 525
Glu Val Leu His Ser Pro Ala Ile Glu Val Arg Val His Cys Gln Leu
        530                 535                 540
Val Arg Leu Phe Ala Arg Gly Ile Glu Glu Asn Pro Lys Pro Asp Ser
545                 550                 555                 560
His Ser

<210> SEQ ID NO 12
<211> LENGTH: 24
<212> TYPE: DNA
<213> ORGANISM: Homo sapiens

<400> SEQUENCE: 12
cgctgcatat cgttgttggg gact                                          24

<210> SEQ ID NO 13
<211> LENGTH: 24
<212> TYPE: DNA
<213> ORGANISM: Homo sapiens
<220> FEATURE:
<223> OTHER INFORMATION: random oligonucleotide

<400> SEQUENCE: 13
cgctgcatat cgttgttggg gact                                          24

<210> SEQ ID NO 14
<211> LENGTH: 24
<212> TYPE: DNA
<213> ORGANISM: Homo sapiens

<400> SEQUENCE: 14
tggtttcgta aatgaccata aata                                          24

<210> SEQ ID NO 15
<211> LENGTH: 24
<212> TYPE: DNA
<213> ORGANISM: Artificial Sequence
<220> FEATURE:
<223> OTHER INFORMATION: random oligonucleotide

<400> SEQUENCE: 15
tcaactgact agatgtacat ggac                                          24
```

<210> SEQ ID NO 16
<211> LENGTH: 4413
<212> TYPE: DNA
<213> ORGANISM: Homo sapiens

<400> SEQUENCE: 16

```
cacgaggccg ctaacggtcc ggcgcccctc ggcgtccgcg cgccccagc  ctggcggacg      60
agcccggcgg cggagatggg ggcgacgggg gcggcggagc cgctgcaatc cgtgctgtgg     120
gtgaagcagc agcgctgcgc cgtgagcctg agcccgcgc  gggctctgct gcgctggtgg     180
cggagcccgg ggcccggagc cggcgccccc ggcgcggatg cctgctctgt gcctgtatct     240
gagatcatcg ccgttgagga acagacgtt  cacgggaaac atcaaggcag tggaaaatgg     300
cagaaaatgg aaaagcctta cgcttttaca gttcactgtg taaagagagc acgacggcac     360
cgctggaagt gggcgcaggt gactttctgg tgtccagagg agcagctgtg tcacttgtgg     420
ctgcagaccc tgcgggagat gctggagaag ctgacgtcca gaccaaagca tttactggta     480
tttatcaacc cgtttggagg aaaaggacaa ggcaagcgga tatatgaaag aaaagtggca     540
ccactgttca ccttagcctc catcaccact gacatcatcg ttactgaaca tgctaatcag     600
gccaaggaga ctctgtatga gattaacata gacaaatacg acggcatcgt ctgtgtcggc     660
ggagatggta tgttcagcga ggtgctgcac ggtctgattg gaggacgca  gaggagcgcc     720
ggggtcgacc agaaccaccc ccgggctgtg ctggtcccca gtagcctccg gattggaatc     780
attcccgcag ggtcaacgga ctgcgtgtgt tactccaccg tgggcaccag cgacgcagaa     840
acctcggcgc tgcatatcgt tgttggggac tcgctggcca tggatgtgtc ctcagtccac     900
cacaacagca cactccttcg ctactccgtg tccctgctgg gctacggctt ctacggggac     960
atcatcaagg acagtgagaa gaacggtgg  ttgggtcttg ccagatacga cttttcaggt    1020
ttaaagacct tcctctccca ccactgctat gaagggacag tgtccttcct ccctgcacaa    1080
cacacggtgg gatctccaag ggataggaag ccctgccggg caggatgctt tgtttgcagg    1140
caaagcaagc agcagctgga ggaggagcag aagaaagcac tgtatggttt ggaagctgcg    1200
gaggacgtgg aggagtggca agtcgtctgt gggaagtttc tggccatcaa tgccacaaac    1260
atgtcctgtg cttgtcgccg gagccccagg ggcctctccc cggctgccca cttgggagac    1320
gggtcttctg acctcatcct catccggaaa tgctccaggt tcaattttct gagatttctc    1380
atcaggcaca ccaaccagca ggaccagttt gacttcactt ttgttgaagt ttatcgcgtc    1440
aagaaattcc agtttacgtc gaagcacatg gaggatgagg acagcgacct caaggagggg    1500
gggaagaagc gctttgggca catttgcagc agccacccct cctgctgctg caccgtctcc    1560
aacagctcct ggaactgcga cggggaggtc ctgcacagcc ctgccatcga ggtcagagtc    1620
cactgccagc tggttcgact ctttgcacga ggaattgaag agaatccgaa gccagactca    1680
cacagctgag aagccggcgt cctgctctcg aactgggaaa gtgtgaaaac tatttaagat    1740
aattattaca gaccaattat gttgatatat acatttaaat gtagaaattt attttgata     1800
gttaaatctt gatttagaa  gaaaccctt  tgtcaacaa  ttttgtgtac atatttggca    1860
ttttcagttc tgtacgcatc tgcgggttgc agcccacgcc gcttactctc agcggatgca    1920
gctgctcact ggggcact   ggcctcttag gttttaacga tgtcaacagt gtagtttaga    1980
aaatggcccg ttagtggctc tattgcaata atgttaggga cattatatga tttccacgca    2040
ggtcacacca tctgggcctg aggtagcagt gggtcacttt gatccacttt gcaggactta    2100
ttctgtaacg gtttgtggcc aagttttggg aagtggttga ttctctttgc cttcatttca    2160
```

```
ccttcctctt cgtttacggt taggacatcg ctgcttgatc cttacaatac tgtgcaactg    2220
caatgcaacg tggccctgct tcaggtgatc cgcgggaggg gcctccacgc cagcgccggg    2280
aaggctgctg ggcctccac acctgcctca tcacggcggc gaggctacga caatccggct    2340
gggagcatga ccttggcgtc tgttctggga gcacagatga taagctctgg aagctggcag    2400
tgtgtaaagc actggcaagt ttgttactgt taaaatgtca aataccaatg ctttatatcg    2460
acgcgaagtg cttaacacag ccgggcttgg gggcagtcag gaggaagctg gccatccgtg    2520
gaggaggggc cggtcctgga ctcccgcagg actcctctga tgcagggcct gaagtctgta    2580
cacgtggtcc agatttgtcc ttgtctttc ttcacactga gttctctata tttattgaac    2640
atcttgtcct tttaagccag agtagtgtaa actgcgtctc ggatgtctgt cttttgcctc    2700
gaagccacga tggatcgctg gtttcctctg cagcgcgagg gctccggcga ccagaggatt    2760
cttcccggaa ggcattcctg ccgcgctccc cggggcaccc ctcaattgtg tactacgtcc    2820
ttgtttagtg tgtatccgtg cccacgtaga tgatgtctgt aacgtagttt tgtttgaaat    2880
atgagaatat gcggcttaaa ctttgatctg taaggagcgg ggccgtggcc gtttggagca    2940
cgctgtagac accgttcctc atgctgccgg gtgggttttg cagaagctcc cttagtgatt    3000
tcatgtttaa caggcagcat ccattttcag aatttcctgg cattgattta tattttgaag    3060
catacaggaa acttctcgtt tcctcgttta gccccaccca gatcaggtga agggcagct     3120 ttaatggtgg ttttatgga ccacattatc agagagcact gtgcaagcca atggttcaa     3180 taatgaatga aaattctggg tgtaaagagt aaatatgccc tggctctttc taccaatgtt    3240
tgctcctggt tggaaagaaa ccaaagattt aagacgggct gctcttccag actggctgtg   3300
cctgcctgtg cccagcaacc tgtgcagccg gcagtgtgcc tggtgtcacg ccaggaggct    3360
gtggctgctg tgggccctct ggaattgtgc tcctcacaaa gtttcccaa aaggttcttc    3420 taagccttta ttgtccctgg taaatgtttc ccggctgggc gcggtggctc acgcctgtaa    3480
tcccagcact ttgggaggcc gaggcgggtg gatcacctaa ggtcaggagt ttgagatcag    3540
cctgcccaac atggtgaaac ctcgtctcta ctaaaaatac acaacttagc cagtcttgtt    3600
ggcgcacgcc tgtaatctca gctactaggg acgctgaggc aggagaatcg cttgaaccca    3660
agaaagaggt ggaggttgcg gtgagccaag attgcgccac tgcactccag cctgggcaaa    3720
cagagggaga ctccatcgcc cccccccaac aaaaaaaaaa gtttcccata cactggcctg    3780
ccccaaaacc cactaacaat tttagcaaaa cagtccaggc caaagaggaa gcatttcatg    3840
ttcaataaga aacccagcca ttccgcatgg ctggttcctg agtggctctg gtgatactct    3900
ccagccacct gctgacattg agaatctcag acctcgggac tgctgttgcg gtaccgtgtg    3960
tctgacacct gccagcagcc cttgtcatc tgcgcgcagg atgggggtga ctgcccagac    4020
attcccgcta gataggctct gatttccggg gcagcctttc agatgcggca gacatacaac    4080
acctgtactt tagagtttta agggaaaaaa atcagaagt gctggttaga tagtaaaaac    4140
ttaggataac ttagaaaggc tagttttagc ttcctttgtg gctccctggt gcaaaacaat    4200
tagcagttat gcaatggacc tgattctagt ttattctaat taagaagtga ggccgagttt    4260
gacttcgttc ctgaatacaa tcttgagtaa ctggaaagt ctgagtgaaa ggatggcctc     4320
attctctttc taatcttgct ggtttcaaga ttagaaaatg gcattatttg atctgaaatg    4380
tttgagaaga cacgaataaa gttacttggg cag                                 4413
```